United States Patent
Sugita et al.

(10) Patent No.: US 8,254,519 B2
(45) Date of Patent: Aug. 28, 2012

(54) X-RAY INSPECTION APPARATUS AND X-RAY INSPECTION METHOD

(75) Inventors: Shinji Sugita, Nara (JP); Noriyuki Kato, Kyotanabe (JP); Masayuki Masuda, Nishinomiya (JP); Tsuyoshi Matsunami, Kyotanabe (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 13/063,253

(22) PCT Filed: Aug. 28, 2009

(86) PCT No.: PCT/JP2009/065064
§ 371 (c)(1),
(2), (4) Date: May 19, 2011

(87) PCT Pub. No.: WO2010/029862
PCT Pub. Date: Mar. 18, 2010

(65) Prior Publication Data
US 2011/0243299 A1 Oct. 6, 2011

(30) Foreign Application Priority Data
Sep. 10, 2008 (JP) .................................. 2008-232354

(51) Int. Cl.
*A61B 6/00* (2006.01)
(52) U.S. Cl. ................. 378/22; 378/21; 378/23
(58) Field of Classification Search ........................ 378/22
See application file for complete search history.

(56) References Cited

U.S. PATENT DOCUMENTS

| 5,757,878 A * | 5/1998 | Dobbs et al. .................... 378/19 |
| 5,841,831 A | 11/1998 | Hell et al. |
| 6,480,564 B1 * | 11/2002 | Kim et al. ....................... 378/21 |
| 6,628,745 B1 | 9/2003 | Annis et al. |
| 2003/0058983 A1 * | 3/2003 | Thayer ............................. 378/19 |

(Continued)

FOREIGN PATENT DOCUMENTS
EP 2239560 A1 10/2010
(Continued)

OTHER PUBLICATIONS

Extended European Search Report issued in corresponding European patent application No. 09813008.1, dated Jan. 18, 2012, 5 pages.

(Continued)

*Primary Examiner* — Alexander H Taningco
(74) *Attorney, Agent, or Firm* — Osha Liang LLP

(57) ABSTRACT

An X-ray inspection apparatus includes a scanning X-ray source for emitting an X-ray, an X-ray detector drive unit having a plurality of X-ray detectors mounted thereon and being capable of independently driving the plurality of X-ray detectors, and an image acquisition control mechanism for controlling the X-ray detector drive unit and acquisition of image data from the X-ray detectors. The scanning X-ray source emits an X-ray by moving an X-ray focal point position of the X-ray source to each of originating point positions of X-ray emission, which are set for the X-ray detectors such that X-rays are transmitted through a plurality of prescribed inspection areas of an inspection object and enter the X-ray detectors. Image pickup by the X-ray detector and movement of another X-ray detector are concurrently performed in an alternate manner. The image acquisition control mechanism acquires image data, and an operation unit reconstructs an image.

12 Claims, 30 Drawing Sheets

U.S. PATENT DOCUMENTS

| | | | |
|---|---|---|---|
| 2005/0157841 A1* | 7/2005 | Chopra | 378/22 |
| 2007/0025497 A1 | 2/2007 | Fujita | |
| 2008/0226023 A1 | 9/2008 | Masuda et al. | |
| 2008/0226035 A1 | 9/2008 | Masuda et al. | |
| 2008/0267347 A1 | 10/2008 | Shimono | |

FOREIGN PATENT DOCUMENTS

| | | | |
|---|---|---|---|
| EP | 2378279 A1 | 10/2011 | |
| JP | 53-132985 A | 11/1978 | |
| JP | 54-002085 A | 1/1979 | |
| JP | 57-200132 A | 12/1982 | |
| JP | 5-076524 A | 3/1993 | |
| JP | 5-269122 A | 10/1993 | |
| JP | 06-177600 A | 6/1994 | |
| JP | 10-043173 A | 2/1998 | |
| JP | 2000-046760 A | 2/2000 | |
| JP | 2003-329616 A | 11/2003 | |
| JP | 2003-344316 A | 12/2003 | |
| JP | 2004-515762 A | 5/2004 | |
| JP | 2004-313391 A | 11/2004 | |
| JP | 2005-241575 A | 9/2005 | |
| JP | 2006-162335 A | 6/2006 | |
| JP | 2008-224448 A | 9/2008 | |
| JP | 2008-224606 A | 9/2008 | |
| JP | 2009-156788 A | 7/2009 | |
| WO | 92/06367 A1 | 4/1992 | |
| WO | 02/46729 A1 | 6/2002 | |
| WO | 2006/131241 A1 | 12/2006 | |
| WO | 2007/051587 A2 | 5/2007 | |

OTHER PUBLICATIONS

Patent Abstracts of Japan, Publication No. 05-076524, dated Mar. 30, 1993, 1 page.
Patent Abstracts of Japan, Publication No. 5-269122, dated Oct. 19, 1993, 1 page.
Patent Abstracts of Japan, Publication No. 10-043173, dated Feb. 17, 1998, 1 page.
Patent Abstracts of Japan, Publication No. 54-002085, dated Jan. 9, 1979, 1 page.
Patent Abstracts of Japan, Publication No. 2004-313391, dated Nov. 11, 2004, 1 page.
Patent Abstracts of Japan, Publication No. 53-132985, dated Nov. 20, 1978, 1 page.
Patent Abstracts of Japan, Publication No. 2008-224448, dated Sep. 25, 2008, 1 page.
Patent Abstracts of Japan, Publication No. 2008-224606, dated Sep. 25, 2008, 1 page.
Patent Abstracts of Japan, Publication No. 2005-241575, dated Sep. 8, 2005, 1 page.
Patent Abstracts of Japan, Publication No. 2009-156788, dated Jul. 16, 2009, 1 page.
Patent Abstracts of Japan, Publication No. 2000-046760, dated Feb. 18, 2000, 1 page.
Patent Abstracts of Japan, Publication No. 2003-344316, dated Dec. 3, 2003, 1 page.
Patent Abstracts of Japan, Publication No. 2003-329616, dated Nov. 19, 2003, 1 page.
Patent Abstracts of Japan, Publication No. 2006-162335, dated Jun. 22, 2006, 1 page.
Patent Abstracts of Japan, Publication No. 06-177600, dated Jun. 24, 1994, 1 page.
Feldkamp, et al., "Practical cone-beam algorithm," Journal of the Optical Society of America, J. Opt. Soc. Am. A/vol. 1, No. 6/Jun. 1984, pp. 612-619, 8 pages.
Andersen, et al., "Simultaneous Algebraic Reconstruction Technique (SART): A Superior Implementation of the Art Algotirum," Ultrasonic Imaging 6 81-94 (1984), 14 pages.
International Search Report issued in PCT/JP2009/065064, mailed on Sep. 29, 2009, with translation, 5 pages.

* cited by examiner

X-RAY INSPECTION APPARATUS AND X-RAY INSPECTION METHOD

BACKGROUND OF INVENTION

1. Technical Field

One or more embodiments of the present invention relate to an X-ray inspection method and an X-ray inspection apparatus. More specifically, one or more embodiments of the present invention relate to an image pickup method for inspecting an object by using X-ray irradiation, which is a technique applicable to an X-ray inspection method and an X-ray inspection apparatus.

2. Background Art

In recent years, LSI (Large-Scale Integration) of higher degree of integration has been developed thanks to microfabrication technique of sub-microns, allowing functions which have conventionally been divided into a plurality of packages to be packed in one LSI. Because conventional QFPs (Quad Flat Packages) and PGAs (Pin Grid Arrays) can no longer accommodate the increased number of pins resulting from incorporating necessary functions in one package, LSIs of BGAs (Ball Grid Arrays) and CSPs (Chip Size Packages) in particular have been used these days. For applications that need to be microminiaturized such as mobile telephones, a BGA package is used even if the number of required pins is not so large.

While BGA and CSP packages of LSI greatly contribute to microminiaturization, soldered portions and the like are not visible from the appearance after being assembled. For this reason, when a printed board and the like having BGA and CSP packages mounted thereon is inspected, a fluoroscopic image obtained by irradiating an inspection object with an X-ray is analyzed, to determine whether or not quality is acceptable.

By way of example, Patent Document 1 (Japanese Patent Laying-Open No. 2000-46760) discloses an X-ray tomographic surface inspection apparatus capable of obtaining a sharp X-ray image by using an X-ray plane detector for detecting a transmitted X-ray.

Patent Document 2 (Japanese Patent Laying-Open No. 2003-344316) discloses a method for reconstructing an image in inclined three-dimensional X-ray CT (Computed Tomography) by arbitrarily selecting an angle of X-ray irradiation.

As shown in FIG. 21, Patent Document 3 (Japanese Patent Laying-Open No. 2003-329616) discloses an image pickup method in which a field of view (inspection object) is rotated during X-ray image pickup. While neither an X-ray source nor a detector needs to be moved during image pickup in this method, the inspection object needs to be rotated for each image pickup in order to change an image pickup angle.

As shown in FIG. 22, Patent Document 4 (Japanese Patent Laying-Open No. 2006-162335) discloses an X-ray inspection apparatus in which two-dimensional inspection is conducted based on an X-ray image obtained by a parallel X-ray detection device, and three-dimensional inspection is conducted based on an X-ray image obtained by inclined X-ray detection means, so that both inspections can be conducted at high speed. A "filtered back-projection method" is proposed as an exemplary reconstruction method. An X-ray image pickup method disclosed in Patent Document 4 is an "image pickup method using a plurality of detectors and a fixed-focal-point X-ray source," and uses a detector arranged for picking up a transmitted image in a perpendicular direction, and a plurality of detectors for picking up transmitted images from different angles while moving on a circular trajectory. Because the X-ray source has a fixed focal point, images of one field of view are picked up from a plurality of angles by moving a substrate.

As shown in FIG. 23, Patent Document 5 (Japanese National Patent Publication No. 2004-515762) discloses an X-ray image pickup method using a scanning X-ray source and one X-ray detector fixed in position.

As shown in FIG. 24, Patent Document 6 (Japanese Patent Laying-Open No. 6-177600) discloses an X-ray image pickup method using an apparatus including a plurality of movable X-ray sources and X-ray detectors as many as the X-ray sources.

[Image Reconstruction Method of X-Ray CT]

As described above, in X-ray CT, based on measured values of an X-ray that has been transmitted through an object and then detected by an X-ray detector, at least a cross-sectional image of the object is reconstructed. Three-dimensional X-ray absorption factor distribution of the object or a part of the object is obtained. Accordingly, an arbitrary cross-sectional image of the object or a part of the object, namely, an image of a plane that crosses a light-receiving surface of the X-ray detector can be eventually reconstructed. An "analytical method" and an "iterative method" are known methods for such reconstruction. These image reconstruction methods are briefly described below.

(Description of X-Ray Projection Data)

FIG. 25 illustrates an image reconstruction method. X-ray image reconstruction is a method for measuring how much an X-ray applied externally of an inspection object has been absorbed (attenuated) by the inspection object from a plurality of different angles, to determine X-ray absorption coefficient distribution inside the inspection object.

The following description is based on the use of a so-called scanning X-ray source as an X-ray source to make a measurement.

Referring to FIG. 25, an X-ray emitted from an X-ray focal point Fa corresponding to an X-ray detector Da is transmitted through an inspection object (not shown) and reaches a pixel Pa of X-ray detector Da. When the X-ray is transmitted through the inspection object, an amount of X-ray (X-ray intensity) is attenuated by the amount corresponding to an X-ray absorption coefficient inherent in each component and the like forming the inspection object. The amount of attenuation in X-ray intensity is recorded as a pixel value of detector pixel Pa.

When the intensity of the X-ray emitted from X-ray focal point Fa is indicated as I, a path of the X-ray from X-ray focal point Fa to detector pixel Pa is indicated as t, and X-ray absorption coefficient distribution of the inspection object is indicated as f(x, y, z), intensity Ia of the X-ray that reaches detector pixel Pa is expressed in the following expression (1).

$$Ia = I \times \exp\{-\smallint f(x,y,z)dt\} \tag{1}$$

Taking logarithms of both sides of this expression, the X-ray absorption coefficient distribution along path t is expressed as a line integral value in the following expression (2). A value obtained by measuring this X-ray absorption coefficient distribution by the X-ray detector is referred to as projection data. Namely, the X-ray detector detects X-ray attenuation amount distribution (or X-ray intensity distribution).

$$\smallint f(x,y,z)dt = \ln(I/Ia) \tag{2}$$

(Description of Analytical Method (e.g., FBP Method: Filtered Back-Projection Method))

As shown in FIG. 25, when an analytical method is used, projection data on intensity Ib of an X-ray which is emitted from a focal point Fb and reaches an X-ray detector Db arranged at a position different from the position of X-ray detector Da is detected for one inspection object (or one part of the inspection object). Such projection data is actually detected with respect to a plurality of positions for one inspection object (or one part of the inspection object), to reconstruct a cross-sectional image of the inspection object based on the projection data.

FIG. 26 shows arrangement of a field of view FOV in the inspection object shown in FIG. 25, a reconstruction pixel V as an object of operation for reconstruction in the field of view FOV, X-ray focal points Fa and Fb, and X-ray detectors Da and Db, when viewed from above. X-rays that have been transmitted through the portion of reconstruction pixel V form images on X-ray detectors Da and Db, which are enlarged in accordance with a ratio of (distance from focal point to reconstruction pixel V) to (distance from focal point to X-ray detector).

Feldkamp et al. proposed a reconstruction algorithm for three-dimensional image reconstruction based on the equation (2). This algorithm (so-called Feldkamp method) is well known as described in Non-Patent Document 1, and thus detailed description thereof will not be provided. A common filtered back-projection method is briefly described below.

Operation of determining X-ray absorption coefficient distribution f(x, y, z) from projection data by adding the projection data along path t followed by an X-ray is referred to as back projection. Because simple addition of the projection data results in blurring due to a peaked-point spread function of an image pickup system, the projection data is filtered. A high-frequency emphasizing filter such as a Shepp-Logan filter is used for this filtering. While a desirable direction of filtering is considered to be a direction perpendicular to a direction of an X-ray transmission path, the Feldkamp method conducts filtering by approximating directions of all projection data transmission paths to the same direction, thereby reconstructing an image that can be inspected.

Steps of image reconstruction in the present embodiment are described below. First, a value pa' obtained by filtering projection data pa of detector pixel Pa of X-ray detector Da is added to a pixel value v of reconstruction pixel V. Further, a value pb' obtained by filtering projection data pb of detector pixel Pb of X-ray detector Db is added to pixel value v of reconstruction pixel V. Consequently, v=pa'+pb' is satisfied. By performing this back-projection operation for all or some of the X-ray detectors, final pixel value v of reconstruction pixel V is expressed in the following expression (3).

$$v = \Sigma(pa' + pb' + \Lambda) \quad (3)$$

By performing this operation for all reconstruction pixels V in a reconstruction area (field of view) FOV, X-ray absorption coefficient distribution of the inspection object is determined, and reconstructed image data is obtained.

FIG. 27 is a flowchart illustrating process steps of such filtered back-projection method.

Referring to FIG. 27, when a process with the analytical method is started (S5002), first, projection data to be processed is selected from projection data on a plurality of picked up images (S5004). Next, the selected projection data is filtered (S5006).

Then, unprocessed reconstruction pixel V in reconstruction field of view FOV is selected (S5008), and a detector pixel corresponding to reconstruction pixel V is determined (S5010).

Then, a filtered pixel value is added to reconstruction pixel V (S5012), and it is determined whether or not addition has been done for all reconstruction pixels (S5014). If the process has not been completed for all reconstruction pixels, the process returns to step S5008, and if the process has been completed, the process proceeds to step S5016.

At step S5016, it is determined whether or not the process has been performed for all projection data. If the process has not been completed for all projection data, the process returns to step S5004. If the process has been completed for all projection data, generation of a reconstructed image ends (S5018).

(Description of Iterative Method (SART))

An iterative method is a method of reconstructing an image by regarding X-ray absorption coefficient distribution f(x, y, z) of an inspection object and projection data In (I/Ia) as an equation.

FIG. 28 is a conceptual diagram showing a concept of a process with the iterative method, when a scanning X-ray source is used. FIG. 29 is a top view of the conceptual diagram of FIG. 28.

Referring to FIGS. 28 and 29, reconstruction steps with the iterative method are described below. A vector v (with an overhead arrow→representing a vector: indicated as "v" in the following text of specification) in which pixel values of a reconstructed image are arranged in a row, and a vector p (with an overhead arrow→representing a vector: indicated as "p" in the following text of specification) in which projection data are arranged in a row are expressed in the following expressions (4) and (5).

In the following, by way of example, a pixel of an image calculated to be formed on X-ray detector Da by an X-ray from X-ray focal point Fa by assuming that reconstruction pixel V has a certain value is referred to as an intermediate projection pixel Qa, and a pixel actually observed on X-ray detector Da is referred to as detector pixel Pa. Similar pixels for X-ray detector Db are referred to as an intermediate projection pixel Qb and detector pixel Pb, respectively.

In the iterative method, for assumed reconstruction pixel vector v and its corresponding intermediate projection data vector q, iterative operation of updating assumed vector v is performed until intermediate projection data vector q can be regarded as matching with projection data of actually measured detector pixel value Pa or Pb, to determine solution v, as described below.

$$\vec{v} = (v_1, v_2, \Lambda, v_J)^T \quad (4)$$

$$\vec{p} = (p_1, p_2, \Lambda, p_I)^T \quad (5)$$

Here, J indicates the number of pixels in the reconstruction area (field of view), and I indicates the number of pixels in the projection data. Further, T indicates transposition. Projection operation for associating v with p is expressed by an I×J coefficient matrix in the following expression (6).

$$W = \{w_{ij}\} \quad (6)$$

Here, image reconstruction with the iterative method can be formulated as a problem of solving the following linear equation (7) to determine v.

$$W\vec{v} = \vec{p} \quad (7)$$

Namely, contribution of vj to pi is defined as wij. It is noted that W indicates degree of contribution of pixel value v of a reconstructed image to pixel value p of projection data, which can be determined based on geometric positions of the X-ray focal point and the X-ray detector, and may be referred to as a detection probability or weight.

Proposed iterative methods include a method for algebraically solving an equation, and a method of considering statistical noise. A commonly used algebraic method of SART (Simultaneous Algebraic Reconstruction Technique) is described below. Details are described in Non-Patent Document 2.

In SART, first, an initial reconstructed image $v^0$ (with an overhead arrow→representing a vector: indicated as "$v^0$→" in the following text of specification) expressed in the following expression (8) is assumed.

$$\vec{v}^0 \quad (8)$$

Initial reconstructed image $v^0$ may be data of all 0, or data obtained from CAD (Computer Aided Design) data and the like may be assumed.

Next, intermediate projection data $q^0$ (with an overhead arrow→representing a vector: indicated as "$q^0$→" in the following text of specification) expressed in the following expression (9) is generated by using projection operation W.

$$\vec{q}^0 = W\vec{v}^0 \quad (9)$$

Intermediate projection data $q^0$ may be generated for one projection data or for a plurality of projection data. The following description is based on generation for one projection data.

Generated intermediate projection data $q^0$ is compared with projection data p obtained from the X-ray detector. Comparison may be made with a method for calculating a difference or a method for performing division. In SART, the difference $(p-q^0)$ is calculated.

Initial reconstructed image $v^0$ is updated. An expression (iterative equation) used for the update is expressed in the following expression (10).

$$v_j^1 = v_j^0 + \frac{\sum_{i=1}^{I} \frac{p_i - q_i}{\sum_{j=1}^{J} w_{ij}} w_{ij}}{\sum_{i=1}^{I} w_{ij}} \quad (10)$$

Calculation time for update can be reduced by calculating the following expressions (11) and (12) in the expression (10) in advance.

$$\sum_{i=1}^{I} w_{ij} \quad (11)$$

$$\sum_{j=1}^{J} w_{ij} \quad (12)$$

A reconstructed image generated by the above calculation is assigned as an initial image, and the same process is repeated several times, whereby reconstructed image data is obtained.

FIG. 30 is a flowchart illustrating a process with the iterative method.

Referring to FIG. 30, when a process with the iterative method is started (S5102), an initial reconstructed image is set (S5104). As described above, all values may be 0 in the initial reconstructed image, for example. Next, projection data to be processed is selected from among a plurality of projection data corresponding to a plurality of X-ray detector positions (S5106).

Intermediate projection data is generated. A method for generating the intermediate projection data has been described above (S5108).

Then, unprocessed reconstruction pixel V in reconstruction field of view FOV is selected (S5110).

A detector pixel corresponding to the reconstruction pixel is determined (S5112).

A value of reconstruction pixel V is updated based on an iterative equation (S5114).

Next, it is determined whether or not update has been done for all reconstruction pixels (S5116). If the process has not been completed for all reconstruction pixels, the process returns to step S5110, and if the process has been completed, the process proceeds to step S5118.

At step S5118, it is determined whether or not the process has been performed for all projection data. If the process has not been completed for all projection data, the process returns to step S5106. If the process has been completed for all projection data, the process proceeds to step S5120.

At S5120, it is determined whether or not the process has been repeated for a predetermined number of times. If the process has not been repeated, the process returns to step S5104 and is repeated by employing a current reconstruction pixel value as an initial reconstructed image. If the process has been repeated for the predetermined number of times, generation of a reconstructed image ends (S5022).

As described above, three-dimensional image of the inspection object can be reconstructed from the projection data obtained by the X-ray detector.

PRIOR ART DOCUMENTS

Patent Documents

Patent Document 1: Japanese Patent Laying-Open No. 2000-46760
Patent Document 2: Japanese Patent Laying-Open No. 2003-344316
Patent Document 3: Japanese Patent Laying-Open No. 2003-329616
Patent Document 4: Japanese Patent Laying-Open No. 2006-162335
Patent Document 5: Japanese National Patent Publication No. 2004-515762
Patent Document 6: Japanese Patent Laying-Open No. 6-177600

Non-Patent Documents

Non-Patent Document 1: L. A. Feldkamp, L. C. Davis and J. W. Kress, "Practical cone-beam algorithm," Journal of the Optical Society of America. A, 612-619 (1984)
Non-Patent Document 2: A. H. Anderson and A. C. Kak, "SIMULTANEOUS ALGEBRAIC RECONSTRUCTION TECHNIQUE (SART): A SUPERIOR IMPLEMENTATION OF THE ART ALGORITHM," ULTRASONIC IMAGING 6, 81-94 (1984)

SUMMARY OF THE INVENTION

In the method shown in FIG. 21 disclosed in Patent Document 3, while neither the X-ray source nor the detector needs to be moved during image pickup, the inspection object needs to be rotated for each image pickup in order to change an image pickup angle, 1) resulting in a circular field of view, so that only a small area can be inspected at a time with a reconstructed image. Further, 2) a stage needs to be moved with a field of view of the inspection object as a rotation center, in order to pick up images of different fields of view.

In the method shown in FIG. 22 disclosed in Patent Document 4, while the plurality of detectors can be simultaneously moved, 1) there is a period of time when the detectors and the X-ray source are not operating because four detectors move simultaneously. 2) A total of five detectors are required (four moving detectors, and one detector dedicated to obtaining a perpendicular transmitted image are required). 3) Because the respective detectors capture different fields of view during single detection operation, timing of reconstruction is delayed (images of one field of view are picked up from a plurality of angles only after a substrate is moved). 4) It takes time to move the detectors because they move on a circular trajectory. Further, with one X-ray focal point, images of the same field of view cannot be picked up with the plurality of detectors without moving an inspection object. Furthermore, because the inclined detector simultaneously moves in order to change an image pickup angle, an image cannot be picked up during a period of this movement.

In the method shown in FIG. 23 disclosed in Patent Document 5, transmitted X-ray images of a plurality of areas are successively obtained. Because the X-ray detector is fixed in position, an inspection object needs to be moved with a stage in order to perform CT image pickup. A transmitted image cannot be picked up during a period of this movement.

In the method shown in FIG. 24 disclosed in Patent Document 6, the X-ray sources/x-ray detector/inspection object advantageously need not be mechanically moved for CT image pickup of one field of view. However, because a stage having the inspection object placed thereon needs to be moved in order to move a field of view of the inspection object, if a plurality of fields of view are inspected, an image cannot be picked up during a period of this movement.

For in-line inspection at a plant, however, one-hundred percent inspection of products is required. Therefore, time required for X-ray inspection needs to be reduced from the viewpoint of manufacturing efficiency.

In conventional X-ray imaging techniques related to X-ray inspection, an image pickup system or work of an inspection object needs to be moved in order to change an inspection area, resulting in a larger number of movable parts. This causes issues with the time required for the X-ray inspection described above, as well as issues of costs for manufacturing drive portions, maintenance and reliability. For example, when a printed board as mentioned above or the like is inspected, a portion to be inspected is often a part of the printed board placed on a stage. In such case, in order to enlarge a resulting X-ray image, an X-ray detector is driven at a position relatively far from the inspection object. Because the portion to be inspected is minute, the image pickup system needs to be driven with extremely high accuracy. For this purpose, a drive mechanism for the image pickup system needs to be capable of picking up necessary images with the smallest possible degree of freedom.

One or more embodiments of the present invention may provide an X-ray inspection apparatus capable of selectively inspecting a prescribed inspection area of an inspection object at high speed, and an X-ray inspection method utilizing such X-ray inspection apparatus.

One or more embodiments of the present invention may provide an X-ray inspection apparatus attaining high maintainability and reliability at low cost by reducing the number of movable parts, and an X-ray inspection method utilizing such X-ray inspection apparatus.

One or more embodiments of the present invention may provide an X-ray inspection apparatus capable of inspecting a plurality of portions of an inspection object at high speed without moving the inspection object, and an X-ray inspection method utilizing such X-ray inspection apparatus.

According to an aspect of one or more embodiments of the present invention, an X-ray inspection apparatus for picking up images of X-rays transmitted from directions that vary with inspection object areas of an object by using a plurality of detector planes, to perform reconstruction processing of an image of the inspection object areas of the object is provided. The X-ray inspection apparatus includes an X-ray detector for picking up images in a plurality of detection positions, detector drive means for moving the X-ray detector to each of the plurality of detection positions, X-ray output means for scanning a focal point and outputting an X-ray, and control means for controlling operation of the X-ray inspection apparatus. The control means includes image acquisition control means for controlling exposure timing of the X-ray detector and the detector drive means, X-ray output control means for controlling the X-ray output means, and image reconstruction process means for reconstructing image data on the plurality of inspection object areas based on data about intensity distribution of the X-rays transmitted through the inspection object areas and picked up by the plurality of detector planes. The image acquisition control means and the X-ray output control means cause the X-ray detector to stop in one of a plurality of image pickup positions, and cause scanning of a focal point of the X-ray output means such that X-rays successively transmitted through the plurality of inspection object areas enter the X-ray detector in that image pickup position and cause image pickup for the different inspection object areas.

According to one or more embodiments of the present invention, the X-ray inspection apparatus may further include a plurality of the X-ray detectors, and movement means for independently moving the X-ray detectors to the image pickup positions. The image acquisition control means and the X-ray output control means cause one of the plurality of X-ray detectors to stop in one of the plurality of image pickup positions, and cause performing of a process of scanning a focal point of the X-ray output means such that X-rays successively transmitted through the plurality of inspection object areas enter the X-ray detector in that image pickup position and cause image pickup for the different inspection object areas in parallel with a process of moving another X-ray detector different from the X-ray detector picking up images to another one of the plurality of image pickup positions.

According to one or more embodiments of the present disclosure, the image reconstruction process means may perform reconstruction processing in parallel with the process of moving the X-ray detector and the process of exposing the X-ray detector by the image acquisition control means and the X-ray output control means.

According to one or more embodiments of the present disclosure, the detector drive means includes single-axis drive means for independently moving the plurality of X-ray detectors along a predetermined single-axis direction.

According to one or more embodiments of the present disclosure, each of the detector planes of the plurality of X-ray detectors has a rectangular shape, and the detector drive means includes rotation means for rotating the plurality of X-ray detectors such that one end of each of the detector planes of each of the plurality of X-ray detectors intersects a direction directed to the X-ray output means in each of the image pickup positions.

According to one or more embodiments of the present disclosure, the image reconstruction process means reconstructs the image data on the inspection object areas with an iterative method.

According to one or more embodiments of the present disclosure, the image reconstruction process means reconstructs the image data on the inspection object areas with an analytical method.

According to another aspect of one or more embodiments of the present invention, an X-ray inspection method for picking up images of X-rays transmitted from directions that vary with inspection object areas of an object by using a plurality of detector planes, to perform reconstruction processing of an image of the inspection object areas is provided. This X-ray inspection method includes the steps of independently moving a plurality of X-ray detectors to a plurality of corresponding image pickup positions, scanning a focal point and outputting an X-ray, stopping one of the plurality of X-ray detectors in one of the plurality of image pickup positions which serves as one of the plurality of detector planes to perform a process of scanning a focal point of X-ray output means such that X-rays successively transmitted through the plurality of inspection object areas enter the X-ray detector in that image pickup position and perform image pickup for the different inspection object areas in parallel with a process of moving another X-ray detector different from the X-ray detector picking up images to another one of the plurality of image pickup positions, and reconstructing image data on the inspection object areas based on data about intensity distribution of the X-rays transmitted through the inspection object areas and detected by the plurality of detector planes.

According to one or more embodiments of the present disclosure, the step of reconstructing image data is performed in parallel with the moving step and the step of performing the process in parallel.

According to one or more embodiments of the present disclosure, in the independently moving step, the plurality of X-ray detectors are independently moved along a predetermined single-axis direction.

According to one or more embodiments of the present disclosure, each of the detector planes of the plurality of X-ray detectors has a rectangular shape, and the X-ray detectors rotate, during moving, such that one end of each of the detector planes of each of the plurality of X-ray detectors intersects a direction directed to the X-ray output means in each of the image pickup positions.

According to one or more embodiments of the present disclosure, in the step of reconstructing image data, the image data on the inspection object areas is reconstructed with an iterative method.

According to one or more embodiments of the present disclosure, in the step of reconstructing image data, the image data on the inspection object areas is reconstructed with an analytical method.

Effects of the Invention

According to the X-ray inspection method and the X-ray inspection apparatus of the one or more embodiments of present invention, a prescribed inspection area of an inspection object can be inspected selectively at high speed.

Further, according to the X-ray inspection method and the X-ray inspection apparatus of one or more embodiments of the present invention, X-ray inspection attaining high maintainability and reliability at low cost by reducing the number of movable parts can be conducted.

Furthermore, according to the X-ray inspection method and the X-ray inspection apparatus of one or more embodiments of the present invention, a plurality of portions of an inspection object can be inspected at high speed.

DETAILED DESCRIPTION

Figure 1:
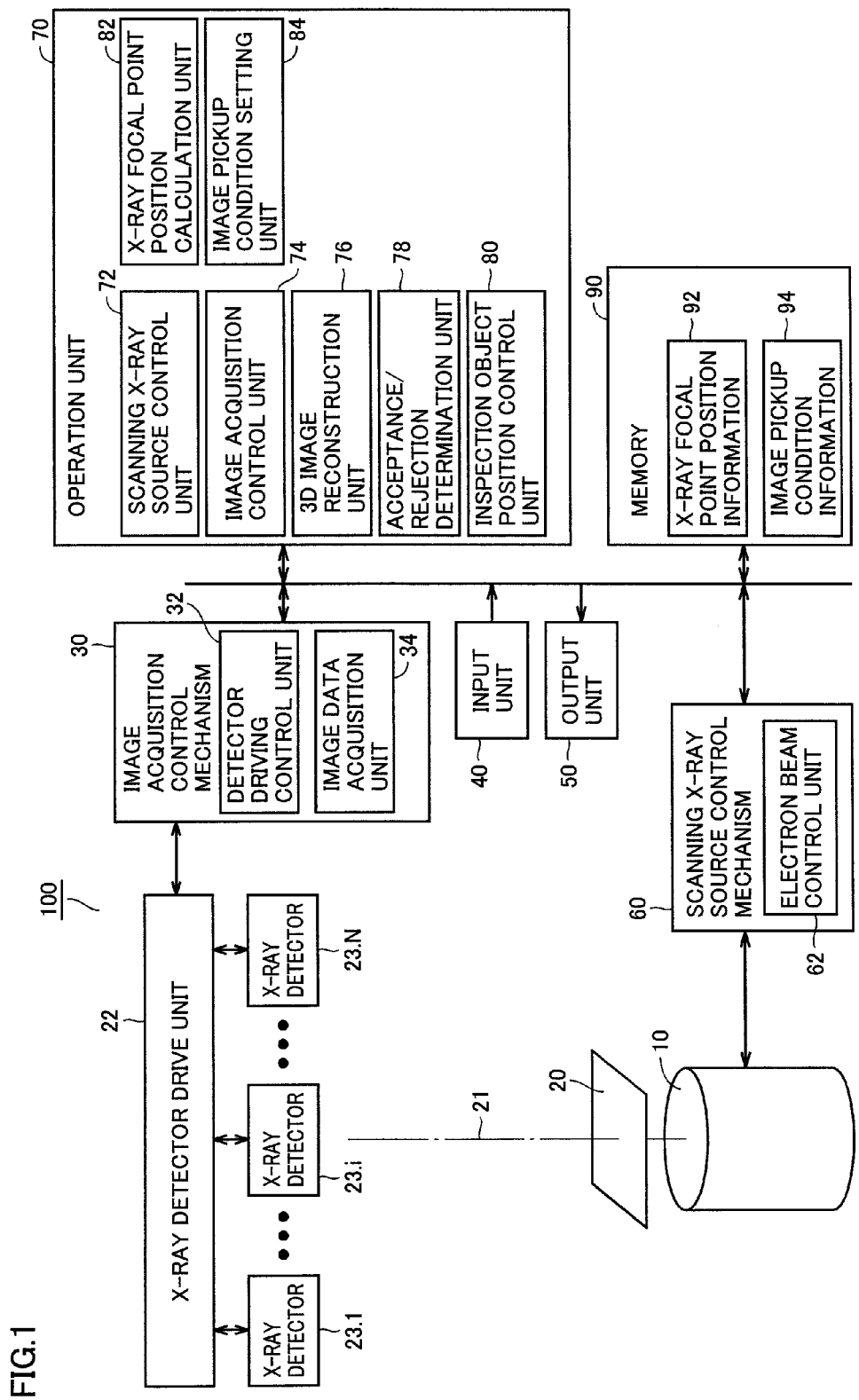
FIG. 1 is a schematic block diagram of an X-ray inspection apparatus according to one or more embodiments of the present invention.

Embodiments of one or more embodiments of the present invention will be described below with reference to the drawings. In the following description, the same components are denoted by the same reference characters. Their names and functions are also the same. Therefore, detailed description thereof will not be repeated. In embodiments of the invention, numerous specific details are set forth in order to provide a more thorough understanding of the invention. However, it will be apparent to one with ordinary skill in the art that the invention may be practiced without these specific details. In other instances, well-known features have not been described in detail to avoid obscuring the invention.

First Embodiment

1. Structure of One or More Embodiments of the Present Invention

FIG. 1 is a schematic block diagram of an X-ray inspection apparatus 100 according to one or more embodiments of the present invention.

Referring to FIG. 1, X-ray inspection apparatus 100 according to one or more embodiments of the present invention is described. It is noted that structures, dimensions, shapes and other relative arrangements described below are not intended to limit the scope of the invention to such features unless specified to the contrary.

X-ray inspection apparatus 100 includes a scanning X-ray source 10 for emitting an X-ray with a shaft 21 as a central shaft, and an X-ray detector drive unit 22 having a plurality of X-ray detectors 23.1 to 23. N mounted thereon, for driving each of X-ray detectors 23.1 to 23.N to a designated position, as will be described later. An inspection object 20 is arranged between scanning X-ray source 10 and X-ray detectors 23.1 to 23.N. X-ray inspection apparatus 100 further includes an image acquisition control mechanism 30 for controlling driving of each of X-ray detectors 23.1 to 23.N by X-ray detector drive unit 22 and acquisition of image data from X-ray detectors 23.1 to 23.N, an input unit 40 for receiving input of an instruction and the like from a user, and an output unit 50 for outputting a measurement result and the like to the outside. X-ray inspection apparatus 100 further includes a scanning X-ray source control mechanism 60, an operation unit 70, and a memory 90. In such structure, operation unit 70 executes a program which is not shown and is stored in memory 90 to control each unit, and performs prescribed operation processing.

Scanning X-ray source 10 is controlled by scanning X-ray source control mechanism 60, and irradiates inspection object 20 with an X-ray.

Figure 2:
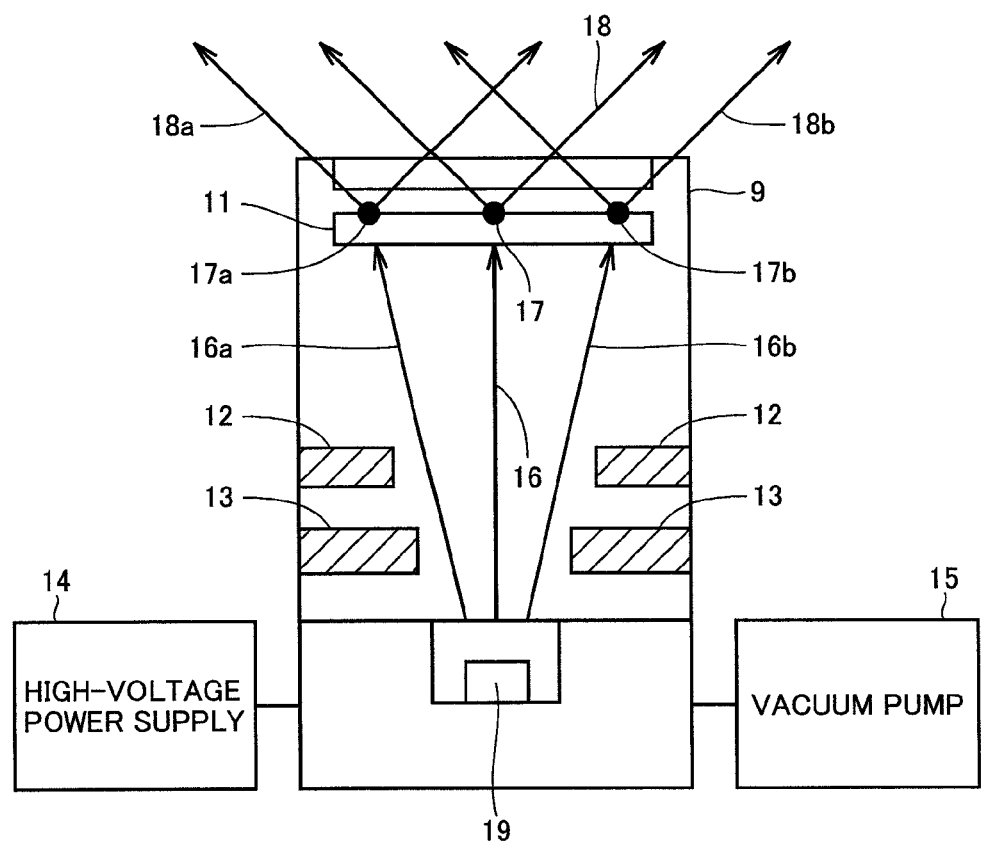
FIG. 2 is a cross-sectional view showing a structure of a scanning X-ray source according to one or more embodiments of the present invention.

FIG. 2 is a cross-sectional view showing a structure of scanning X-ray source 100.

In a general industrial X-ray fluoroscope, if an inspection object is minute, it is desirable to obtain a fluoroscopic X-ray image enlarged as much as possible. For this purpose, a focal point where an X-ray is generated needs to be extremely small. Thus, a microfocus X-ray source, which is a transmissive X-ray source having a focal point dimension of a few μm, is used. Scanning X-ray source 10 in FIG. 2 is a microfocus X-ray source capable of scanning a focal point position.

Referring to FIG. 2, in scanning X-ray source 10, an electron gun 19 controlled by an electron beam control unit 62 irradiates a target 11 such as tungsten with an electron beam 16. An X-ray 18 is then generated from a position where electron beam 16 impinged on the target (X-ray focal point position 17), and is emitted (output). An electron beam system is housed in a vacuum container 9. Inside of vacuum container 9 is kept evacuated by a vacuum pump 15, and electron beam 16 accelerated by a high-voltage power supply 14 is emitted from electron gun 19.

In scanning X-ray source 10, electron beam 16 is converged by an electron beam convergence coil 13, and then deflected by a deflection yoke 12, so that a position where electron beam 16 impinges on target 11 can be arbitrarily changed. For example, an electron beam 16a deflected by deflection yoke 12 impinges on target 11, and an X-ray 18a is output from an X-ray focal point position 17a. Similarly, an electron beam 16b deflected by deflection yoke 12 impinges on target 11, and an X-ray 18b is output from an X-ray focal point position 17b. In one or more embodiments of the present invention, scanning X-ray source 10 is a transmissive source unless otherwise specified. As will be described later, it is desirable for a target to have a continuous surface rather than a ring shape, in order to improve degree of freedom for setting a position which should be the originating point of X-ray emission set in accordance with a portion to be inspected of an inspection object (hereinafter referred to as "originating point position of X-ray emission") when generating an X-ray from the position. In the following description, the position will simply be indicated collectively as X-ray focal point position 17, unless specified in terms of position.

When moving an X-ray focal point position to each originating point position of X-ray emission described above, a position of the X-ray source itself can be mechanically moved each time. With the structure such as shown in FIG. 2, however, an X-ray focal point position can be moved to the originating point position of X-ray emission within a certain range without mechanically moving the X-ray source, thereby realizing an X-ray inspection apparatus having high maintainability and reliability.

Stated another way, the "originating point position of X-ray emission" means a spatial position that can be determined upon determination of a spatial position of an X-ray detector 23.*i* (i being a specific one from 1 to N) used for image pickup and a spatial position of a portion to be inspected of inspection object 20, and the X-ray focal point position means a position on a target to which an X-ray is actually output. Therefore, the X-ray focal point position is brought to the "originating point position of X-ray emission" by the scanning X-ray source scanning an electron beam.

Returning to FIG. 1, scanning X-ray source control mechanism 60 includes electron beam control unit 62 for controlling output of an electron beam. Electron beam control unit 62 receives designation of an X-ray focal point position, and X-ray energy (tube voltage, tube current) from operation unit 70. The X-ray energy varies with a structure of an inspection object.

Inspection object 20 is arranged between scanning X-ray source 10 and an X-ray detector 23 (hereinafter "X-ray detectors 23.1 to 23.N" being collectively referred to as "X-ray detector 23"). Inspection object 20 may be moved to an arbitrary position on an X-Y-Z stage, or may be moved in one direction such as a belt conveyor to be arranged in a position for inspection. If an inspection object is as small as a printed board, the inspection object may be moved while scanning X-ray source 10 and X-ray detector 23 are fixed. If an inspection object has a large area as in the case of a glass substrate and it is difficult to arbitrarily move the inspection object, scanning X-ray source 10 and X-ray detector 23 may be moved while being fixed in relative position to each other.

X-ray detector 23 is a two-dimensional X-ray detector for detecting an X-ray output from scanning X-ray source 10 and transmitted through inspection object 20, and forming an image. X-ray detector 23 may be a CCD (Charge Coupled Device) camera or an I.I. (Image Intensifier) tube, for example. In one or more embodiments of the present invention where the plurality of X-ray detectors are arranged on X-ray detector drive unit 22, X-ray detector 23 is desirably an FPD (flat panel detector) having good space efficiency. Further, X-ray detector 23 desirably has high sensitivity so that it can be used for in-line inspection, and particularly desirably is a direct conversion FPD using CdTe.

A detailed structure of X-ray detector drive unit 22 will be described later.

Image acquisition control mechanism 30 includes a detector driving control unit 32 for controlling X-ray detector drive unit 22 to move X-ray detector 23 to a position designated by operation unit 70, and an image data acquisition unit 34 for acquiring image data of X-ray detector 23 designated by operation unit 70. As will be described later, one or a plurality of X-ray detectors may be simultaneously designated to acquire image data from operation unit 70 depending on a situation of image pickup.

A position of X-ray detector 23 driven by X-ray detector drive unit 22 can be seen from a position sensor (not shown), and can be provided into operation unit 70 through detector driving control unit 32.

Further, it is desirable for X-ray detector drive unit 22 to be vertically movable to adjust magnifying power. In this case, a position of X-ray detector drive unit 22 in a vertical direction can be seen from a sensor (not shown), and can be provided into operation unit 70 through detector driving control unit 32.

Input unit 40 is an operation input device for receiving input from the user.

Output unit 50 is a display for displaying an X-ray image and the like formed by operation unit 70.

Namely, the user can input various items through input unit 40, and various operation results obtained by processing of operation unit 70 are displayed on output unit 50. An image displayed on output unit 50 may be output for visual acceptance/rejection determination by the user, or may be output as a result of acceptance/rejection determination made by an acceptance/rejection determination unit 78 to be described later.

Operation unit 70 includes a scanning X-ray source control unit 72, an image acquisition control unit 74, a 3D image reconstruction unit 76, acceptance/rejection determination unit 78, an inspection object position control unit 80, an X-ray focal point position calculation unit 82, and an image pickup condition setting unit 84.

Scanning X-ray source control unit 72 determines an X-ray focal point position and X-ray energy, and transmits a command to scanning X-ray source control mechanism 60.

Image acquisition control unit 74 determines X-ray detector(s) 23 driven by X-ray detector drive unit 22 to a designated position(s) to acquire an image, and transmits a command to image acquisition control mechanism 30. Image acquisition control unit 74 also acquires image data from image acquisition control mechanism 30.

Then, 3D image reconstruction unit 76 reconstructs three-dimensional data from a plurality of image data acquired by image acquisition control unit 74.

Acceptance/rejection determination unit 78 determines whether or not an inspection object is acceptable based on the 3D image data reconstructed by 3D image reconstruction unit 76, or fluoroscopic data. For example, acceptance/rejection determination unit 78 recognizes a shape of a solder ball, and determines whether or not the ball is acceptable by determining whether or not the shape is within a predetermined tolerable range. An algorithm for the acceptance/rejection determination, or input information to the algorithm varies with an inspection object, and is thus obtained from image pickup condition information 94.

Inspection object position control unit 80 controls a mechanism (not shown) for moving inspection object 20, such as a stage.

X-ray focal point position calculation unit 82 calculates an X-ray focal point position, an irradiation angle and the like for an inspection area of inspection object 20, when inspecting the inspection area. Details will be described later.

Image pickup condition setting unit 84 sets conditions for outputting an X-ray from scanning X-ray source 10, depending on inspection object 20. The conditions include a voltage applied to the X-ray source, image pickup time, and the like.

Memory 90 includes X-ray focal point position information 92 storing the X-ray focal point position calculated by X-ray focal point position calculation unit 82, image pickup condition information 94 storing the image pickup conditions set by image pickup condition setting unit 84 and information about the algorithm for acceptance/rejection determination, and a program for realizing the functions performed by operation unit 70 described above. Memory 90 is only required to accumulate data, and is formed of a storage device such as a RAM (Random Access Memory), an EEPROM (Electrically Erasable and Programmable Read-Only Memory), or an HDD (Hard Disc Drive).

(First Structure of X-Ray Detector Drive Unit 22: Structure for Independent Movement of Detectors)

In X-ray inspection apparatus 100, a relation of (number of X-ray detectors)<<(number of picked up images required for reconstruction) is satisfied. This is because it is generally impractical from the viewpoint of costs of FPDs to provide detectors as many as images required to be picked up. Therefore, when a larger number of images than X-ray detectors are picked up, the (X-ray detectors)/(X-ray source)/(stage having inspection object placed thereon) needs to be mechanically moved. An image pickup process cannot be performed during such mechanical movement.

As will be described below, X-ray inspection apparatus 100 according to the first embodiment allows reduction in this vacant time that does not contribute to improvement in speed of the entire system.

(Time Loss in Image Pickup Process Resulting from Mechanical Movement)

In the following, before describing the structure and operation of X-ray inspection apparatus 100 according to the first embodiment, a general structure of a movement mechanism portion allowing mechanical movement of an image pickup system or an inspection object in a possible X-ray inspection apparatus will be described.

Time required for X-ray tomographic image pickup is i) time for mechanical movement of constituent elements for image pickup ((X-ray detector)/(X-ray source)/(stage having inspection object placed thereon)), ii) time for picking up a transmitted X-ray image (exposure time of sensor), and iii) image reconstruction and inspection time.

The ii) time for picking up a transmitted X-ray image can be reduced by increasing luminance of the X-ray source and increasing sensitivity of the X-ray detector, and the iii) image reconstruction and inspection time can be reduced by enhancing performance of an information processing device.

The i) time for mechanical movement of constituent elements can be reduced by the structure and operation of X-ray inspection apparatus 100.

Therefore, X-ray inspection apparatus 100 uses 1) two or more X-ray detectors that can be independently moved, and 2) a scanning X-ray source capable of freely changing a position of a focal point on a target as an X-ray source, as will be described below.

With this structure, time required for inspection can be reduced not only for the case of (time required for picking up one transmitted X-ray image)≈(time for mechanical movement), but also for the case of (time for mechanical movement)>>(time for picking up one image (sensor exposure)).

To reduce time required for inspection, a "field of view" needs to be considered as well. Namely, CT image pickup needs to be performed not for one field of view but for a plurality of fields of view for actual inspection. If an inspection object is a QFP of 40×40 mm, for example, the inspection object may need to be divided into four fields of view for image pickup (one field of view is 20×20 mm).

Figure 3:
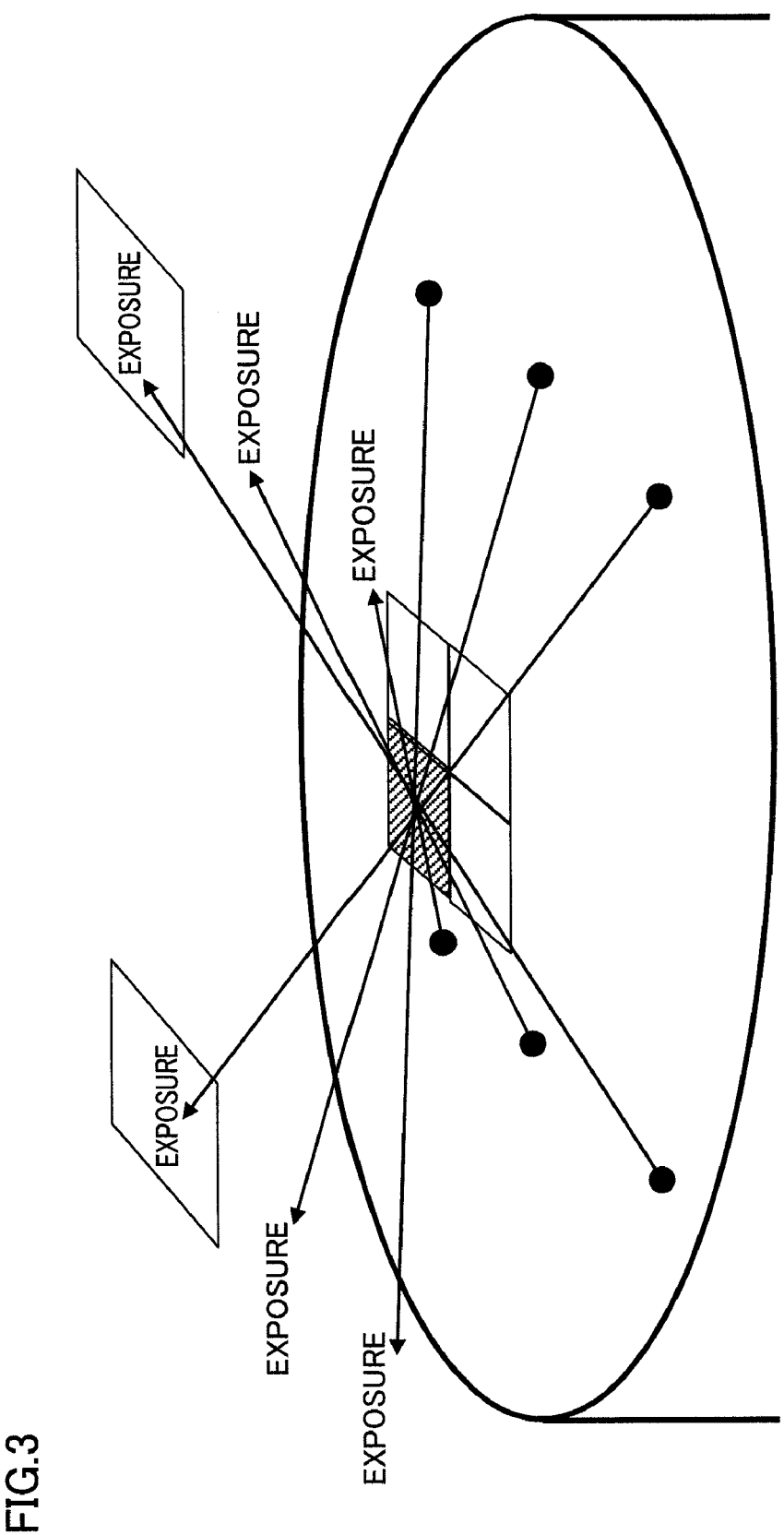
FIG. 3 schematically illustrates a method of picking up images of a plurality of fields of view by using a scanning X-ray source according to one or more embodiments of the present invention.

FIG. 3 schematically illustrates a method for picking up images of a plurality of fields of view by using a scanning X-ray source.

With a structure such as shown in FIG. 3 of picking up images of one field of view position from a plurality of directions and then picking up images of the next field of view, a sensor needs to be moved for each exposure period, resulting in loss in process which corresponds to time for mechanical movement of the constituent elements for image pickup.

In general, when a tomographic image of a large area of interest in an inspection object is picked up (CT image pickup: Computer Tomography) with a two-dimensional X-ray detector, images are picked up by dividing an object area into a plurality of sections, and image reconstruction is performed for each divided section. Each of the divided sections of the area of interest is referred to as a "field of view." The "CT image pickup" is defined as "picking up a plurality of transmitted X-ray images from different angles, which are required for inspection of a reconstructed image."

Figure 4:
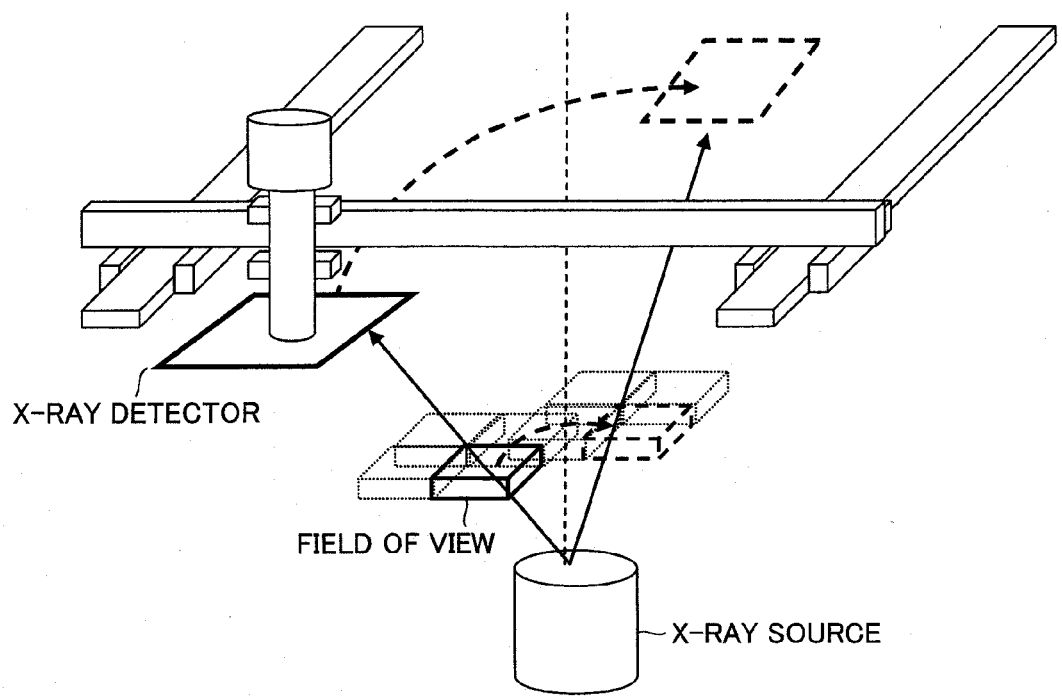
FIG. 4 is a conceptual diagram showing an example of a movement mechanism for CT image pickup according to one or more embodiments of the present invention.

FIG. 4 is a conceptual diagram showing an example of a movement mechanism for such CT image pickup. In FIG. 4, an X-ray detector is mechanically translated in an X-Y plane and rotated in a θ direction, and a field of view (inspection portion of an inspection object) is also translated in the X-Y plane, to obtain a plurality of picked up images required for reconstruction.

As will be described in detail below, in the example of FIG. 4, an image pickup system or the inspection object is mechanically moved in order to obtain a plurality of picked up data. Because an image cannot be picked up during such movement, time for this movement has been an obstacle to increase in speed of the system.

Figure 5:
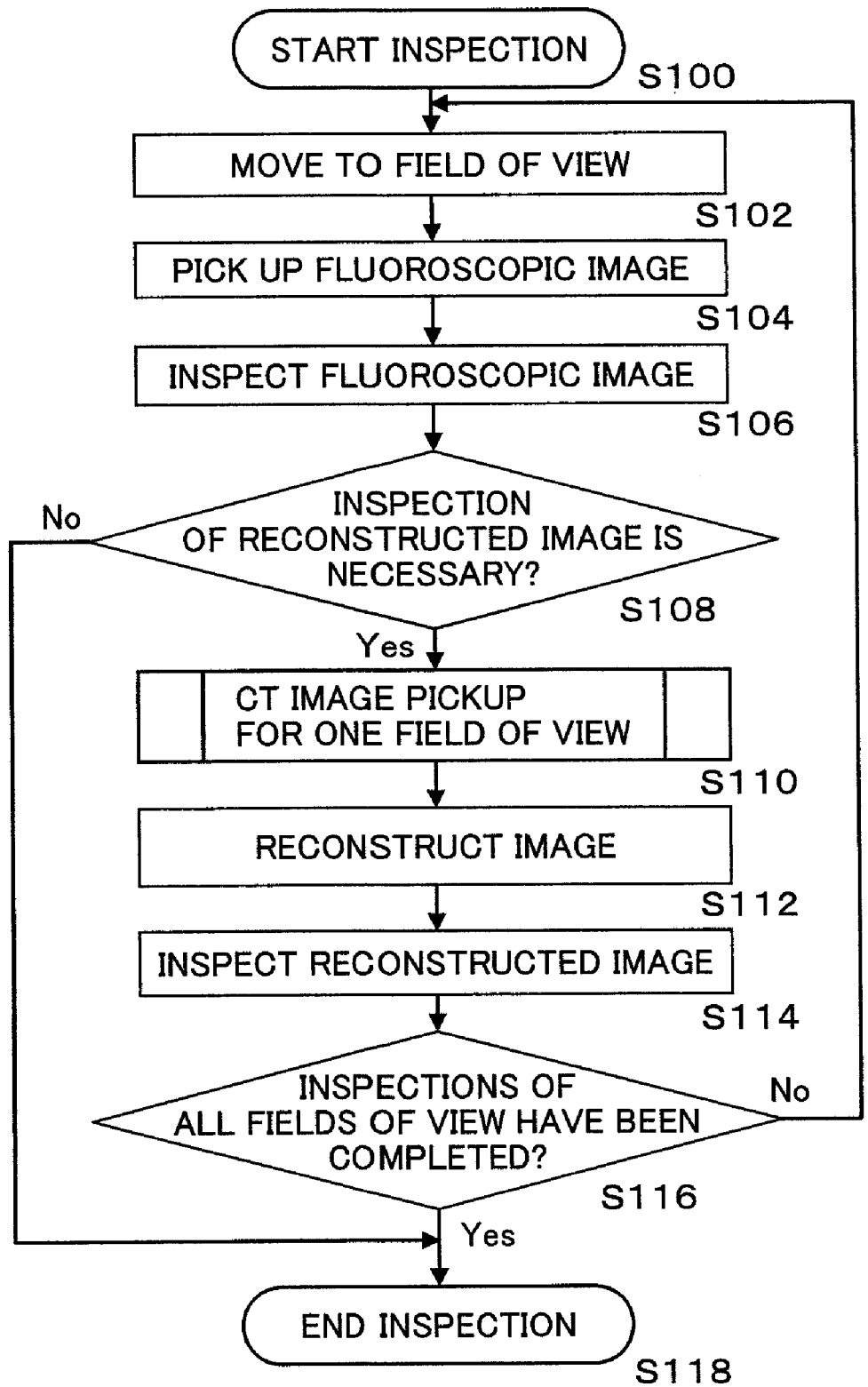
FIG. 5 is a flowchart of overall inspection of a reconstructed image by the movement mechanism shown in FIG. 4 according to one or more embodiments of the present invention.

FIG. 5 is a flowchart of overall inspection of a reconstructed image by the movement mechanism shown in FIG. 4.

Referring to FIG. 5, when a process is started (S100), first, an inspection portion (field of view) of an inspection object is moved to a position where an image of the inspection portion can be picked up (S102). Namely, a stage having the inspection object placed thereon and the X-ray detector are moved to predetermined positions in order to pick up a fluoroscopic image.

Then, a fluoroscopic image is picked up (S104), and the fluoroscopic image is inspected to determine whether or not a field of view of the inspection object (scope picked up in the fluoroscopic image) is acceptable based on the acquired fluoroscopic image (S106).

Next, it is determined whether or not inspection with a reconstructed image is necessary (S108).

If inspection with a reconstructed image is unnecessary, the inspection ends (S118).

If inspection with a reconstructed image is necessary, CT image pickup for one field of view is then performed (S110). During the CT image pickup, images of the field of view in the inspection object (reconstruction area or area similar to the scope picked up in the fluoroscopic image described above) are picked up from a plurality of directions.

Next, a reconstructed image is generated from the images picked up from the plurality of directions (S112). Then, acceptance/rejection determination is made with the reconstructed image (S114).

Then, it is determined whether or not inspections of all fields of view have been completed (S116). If the inspections have not been completed, the process returns to step S102. If the inspections of all fields of view have been completed, the inspection ends (S118).

Figure 6:
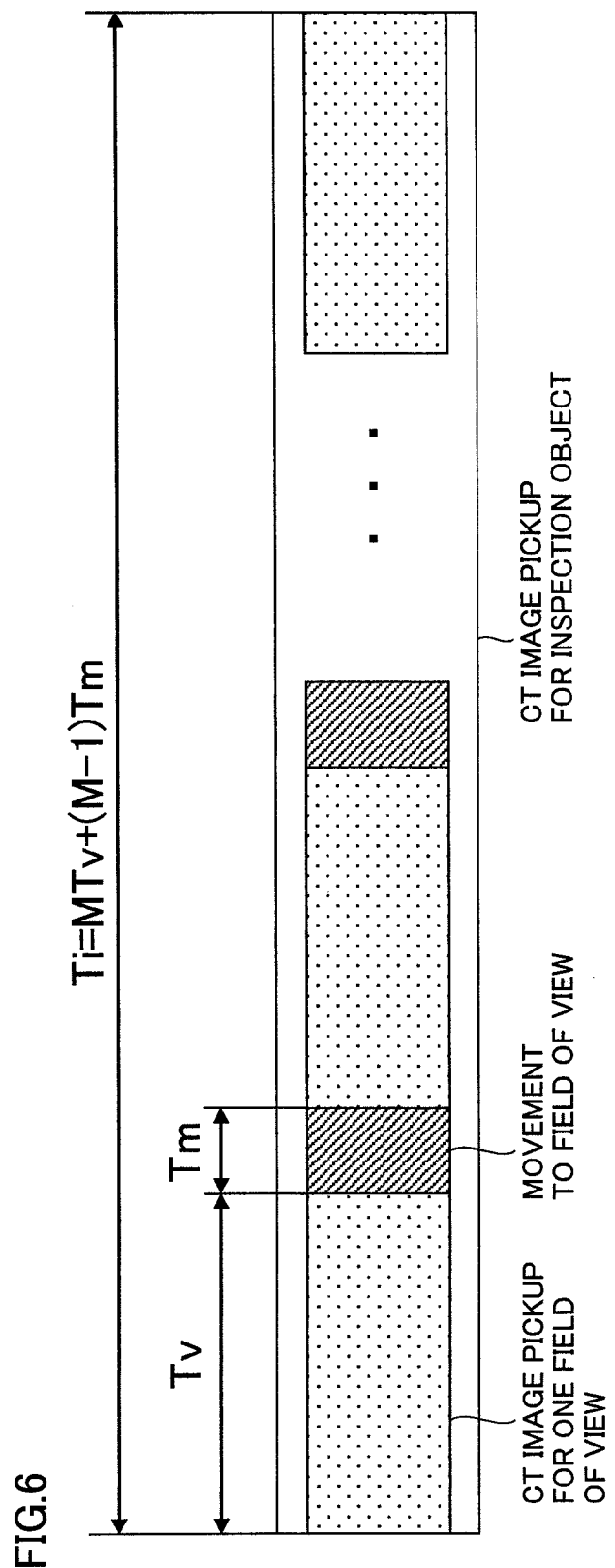
FIG. 6 is a timing chart of the overall inspection according to the flowchart illustrated in FIG. 5 according to one or more embodiments of the present invention.

FIG. 6 is a timing chart of the overall inspection according to the flowchart illustrated in FIG. 5.

In the following description, the inspection object is divided into M (e.g., four) fields of view, and N images are picked up during CT image pickup. Signs are defined below.

Here, time for picking up images of the entire inspection object is indicated as Ti, time for picking up images of one field of view is indicated as Tv, time required for mechanical movement (movement of stage, X-ray detector and the like) is indicated as Tm, and time for image pickup (exposure of X-ray detector) is indicated as Ts.

As shown in FIG. 6, time Ti for CT image pickup of the entire inspection object is a sum of time for picking up images of M fields of view and times Tm for mechanical movement (time for movement to field of view) for (M−1) times, and is thus expressed in the following expression (13).

$$Ti=MTv+(M-1)Tm \quad (13)$$

Figure 7:
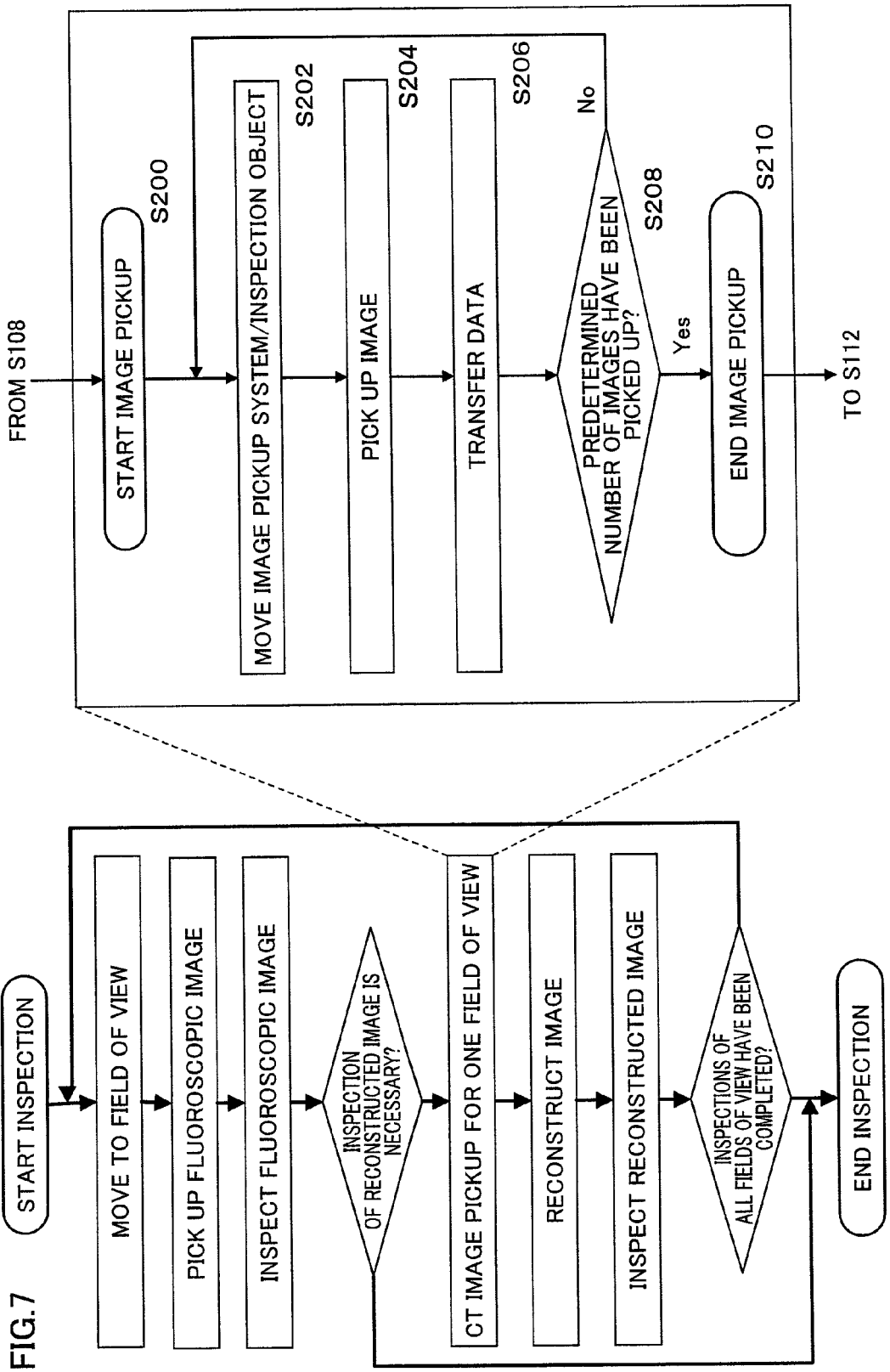
FIG. 7 is a flowchart illustrating a process of CT image pickup for one field of view illustrated in FIG. 5 according to one or more embodiments of the present invention.

FIG. 7 is a flowchart illustrating a process of CT image pickup for one field of view illustrated in FIG. 5.

Referring to FIG. 7, when CT image pickup for one field of view is started (S200), first, the image pickup system and/or the inspection object are/is moved to an image pickup position(s) for a current field of view (S202). The image pickup position can be automatically calculated from design information such as CAD data. Because the inspection object is placed on the stage, the field of view can be moved with movement or rotation of the stage.

Next, an image of the field of view portion in the inspection object is picked up (S204). Data on the picked up image on the inspection object can be obtained by emitting an X-ray from the X-ray source and exposing the X-ray detector. Time for exposure can be predetermined based on a size of the inspection object, intensity of the X-ray generated from the X-ray source, and the like.

Next, the data on the image picked up by the X-ray detector is transferred to the operation unit (S206). Namely, in order to reconstruct an image, the data on the picked up image is transferred to the operation unit for performing reconstruction processing.

Next, it is determined whether or not a predetermined number of images have been picked up (S208). The predetermined may be determined from design information such as CAD data before inspection, or may be determined by a visual check by an operator. If the predetermined has been reached, CT image pickup ends (S210), and the image reconstruction process (S112 of FIG. 5) is performed. If the predetermined has not been reached, the process returns to step S202 where the image pickup system and/or the inspection object are/is moved again for picking up images of the field of view from the next image pickup position.

Figure 8:
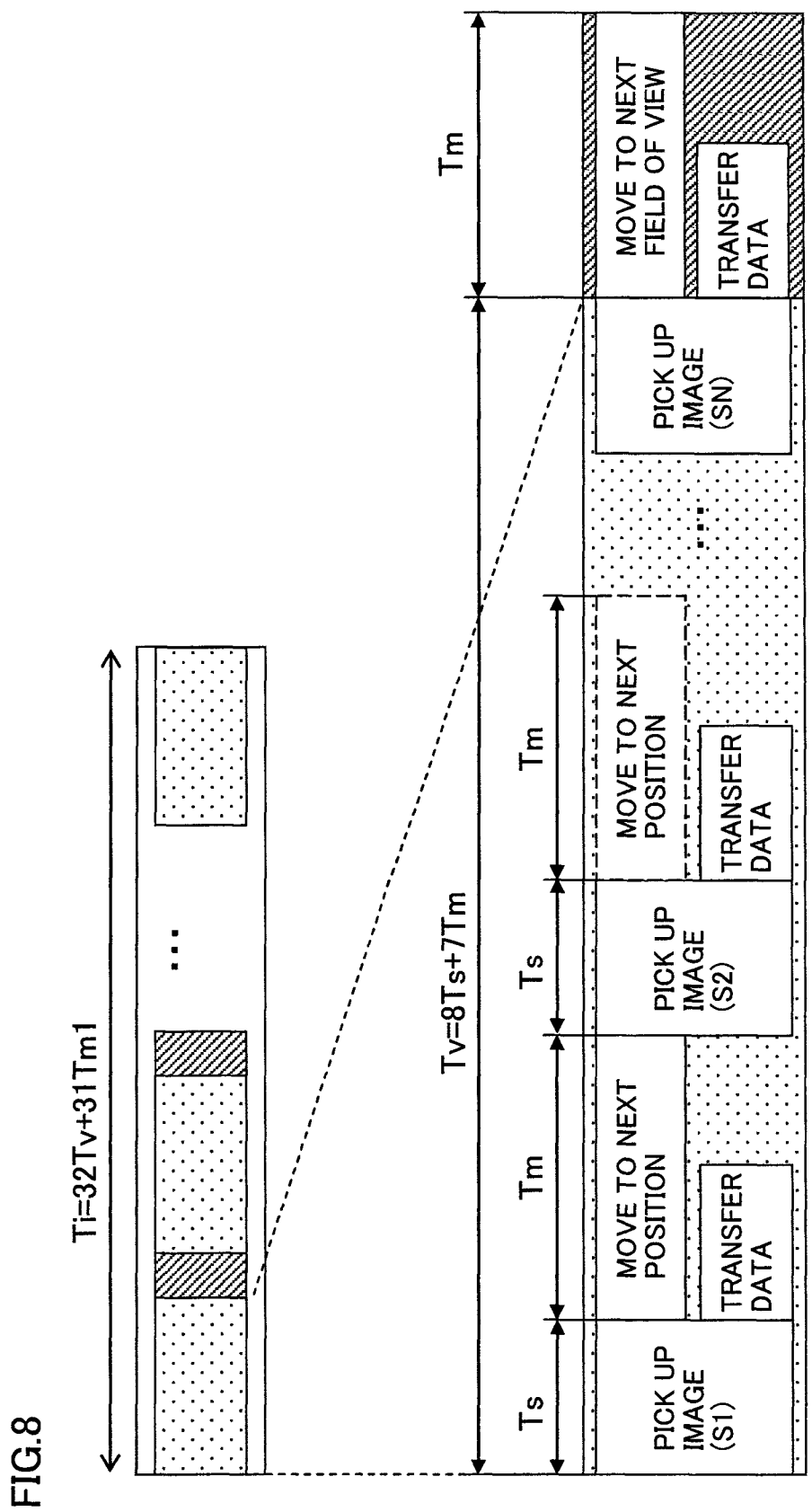
FIG. 8 is a timing chart of a process of picking up images from a plurality of directions (eight directions in this case), in the process of CT image pickup for four fields of view illustrated in FIG. 7 according to one or more embodiments of the present invention.

FIG. 8 is a timing chart of a process of picking up images from a plurality of directions (eight directions in this case), in the process of CT image pickup for four fields of view illustrated in FIG. 7.

Here, there are S (one in FIG. 4) X-ray detectors mounted on one circular rotation mechanism in a structure such as shown in FIG. 4, and the X-ray detectors are rotated together by a detector rotation mechanism. It is noted that one image is picked up by one X-ray detector.

As shown in FIG. 8, time Tv for CT image pickup for one field of view by an X-ray detector is a sum of times Ts for image pickup for N times (indicated as S1, S2, . . . SN in the figure: N=8 in this case) and time for necessary mechanical movement, and is thus expressed in the following expression (14), for example.

$$\text{When there is one detector: } Tv=8Ts+7Tm \quad (14)$$

Here, data on picked up images is transferred simultaneously with mechanical movement.

Accordingly, when the above process is performed for four fields of view, total image pickup time is expressed as below.

$$Ti=32Ts+31Tm$$

In the structure for image pickup such as shown in FIG. 4, the stage having the inspection object placed thereon needs to be mechanically moved for CT image pickup for a plurality of fields of view. A transmitted image cannot be picked up while the constituent elements for image pickup are mechanically moved in accordance with a field of view. In this method, therefore, (time for moving field of view), namely, (time for mechanical movement) has been an obstacle to increase in speed of the entire system.

(Sequence of Image Pickup Process of X-Ray Inspection Apparatus 100)

In order to eliminate the obstacle to increase in speed as described with reference to FIGS. 3 to 8, X-ray inspection apparatus 100 employs an image pickup sequence using scanning X-ray source 10 and the plurality of independently movable X-ray detectors 23, to successively pick up images of a plurality of fields of view with one detector while mechanically moving another detector.

Figure 9:
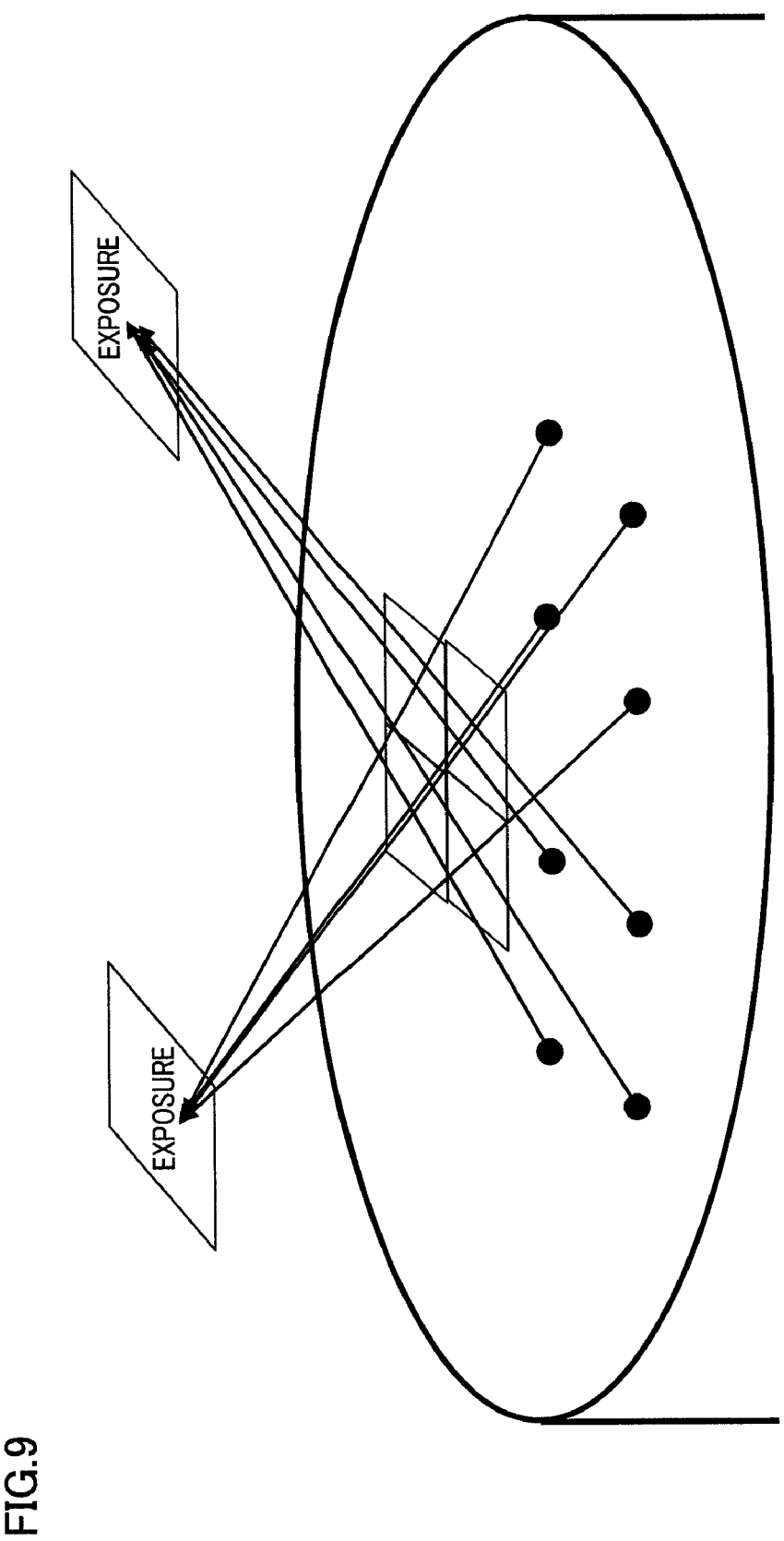
FIG. 9 illustrates a concept of an image pickup process sequence in an X-ray inspection apparatus according to one or more embodiments of the present invention.

FIG. 9 illustrates a concept of the image pickup process sequence of X-ray inspection apparatus 100.

Namely, in the sequence of the image pickup process of X-ray inspection apparatus 100, images of a plurality of fields of view are picked up with regard to one sensor position, and then images of the plurality of fields of view are picked up with regard to the next sensor position.

With such sequence, a detector can be moved while images of the plurality of fields are picked up, thereby reducing load on the movement mechanism. Further, a total number of movements required for one inspection object can also be reduced.

This is because of the following reasons.

i) If a large object area in an inspection object is divided into a plurality of fields of view in order to pick up fine images of the area, transmitted X-ray images of the plurality of fields of view are picked up without taking time to mechanically move constituent elements for moving the field of view.

ii) If an X-ray detector needs to be mechanically moved in order to perform CT image pickup, time for mechanical movement during which an image pickup process cannot be performed is reduced.

Such sequence is effective when time required for image pickup (exposure) and time required for operation processing for reconstruction are reduced, and a relation of (time for mechanical movement of constituent elements for image pickup)>>(time for one image pickup (sensor exposure)) is satisfied.

Structure and Operation of X-Ray Inspection Apparatus 100 in First Embodiment

The structure and operation of X-ray inspection apparatus 100 in the first embodiment are described in detail below.

X-ray inspection apparatus 100 in the first embodiment has the following structure.

1) X-ray detector drive unit 22 is provided with at least two or more X-ray detectors 23, and is configured to be able to independently move X-ray detectors 23.

2) Scanning X-ray source 10 capable of freely changing a position of a focal point on a target is used as an X-ray source.

3) Any one of an analytical method and an iterative method can be used as an algorithm for image reconstruction.

Figure 10:
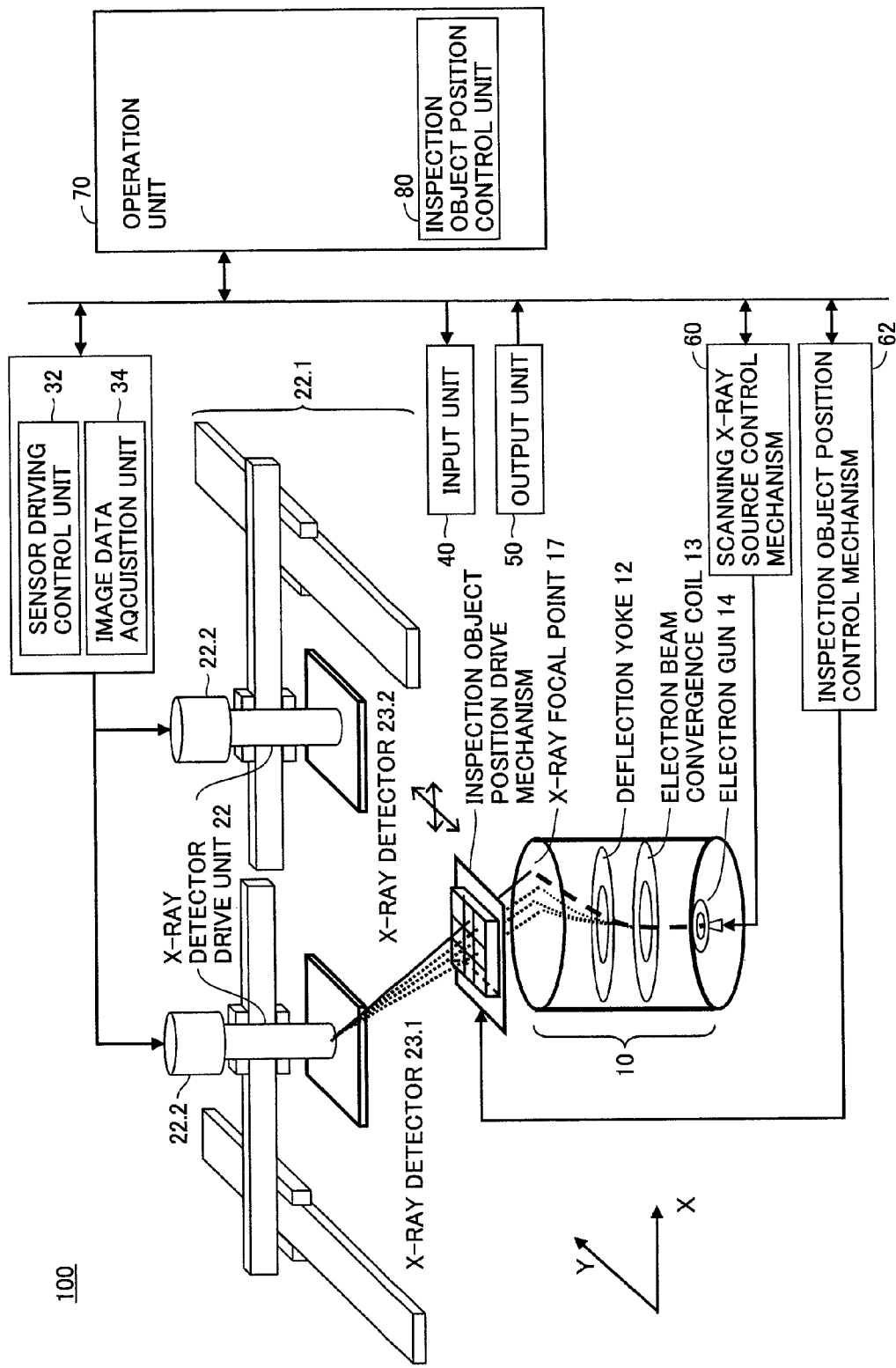
FIG. 10 illustrates a structure of an X-ray inspection apparatus according to a first embodiment.

FIG. 10 illustrates a structure of X-ray inspection apparatus 100 in the first embodiment. The same parts as those in FIG. 1 are denoted by the same reference characters, and portions necessary for description are extracted and illustrated from portions directly related to control of an X-ray focal point position, control of an X-ray detector position, control of an inspection object position, and the like.

Referring to FIG. 10, X-ray detector drive unit 22 is an XYθ operation mechanism capable of driving X-ray detectors 23.1 and 23.2 with a degree of freedom in XYθ, and a scanning X-ray source is used as X-ray source 10.

In the structure shown in FIG. 10, an inspection object position drive mechanism (e.g., X-Y stage) having an inspection objected fixed thereon and capable of two-dimensional movement and inspection object position control unit 80 are provided for moving a position of the inspection object.

While two independently movable X-ray detectors are used in FIG. 10, more than two X-ray detectors may be provided.

X-ray detector 23.1 and X-ray detector 23.2 are independently capable of X-Y-θ operation. As will be described later, the mechanism for θ rotation may not always be provided depending on a method for driving X-ray detector 23. Positions of X-ray detector 23.1 and X-ray detector 23.2 can also be changed in a Z direction by an actuator of X-ray detector drive unit 22, and magnifying power of a transmitted image can be adjusted by changing the positions in the Z direction.

X-ray detector drive unit 22 includes an orthogonal biaxial robot arm 22.1 and a detector support unit 22.2 having an axis of rotation, and moves and rotates X-ray detector 23. It is noted that any other mechanism having a structure allowing movement in the X-Y direction or θ rotation in the X-Y plane and having similar functions with respect to movement of X-ray detector 23 may be used.

A field of view of the inspection object is capable of X-Y movement independently of X-ray detector 23.1 or 23.2, by the inspection object position drive mechanism controlled by inspection object position control unit 80 in operation unit 70. Further, as described above, the scanning X-ray source as X-ray source 10 can move X-ray focal point position 17 to an arbitrary position on the X-ray target at high speed.

Operation unit 70 transmits instructions to detector driving control unit 32, image data acquisition unit (X-ray detector controller) 34, and scanning X-ray source control mechanism 60, and executes a program illustrated in a flowchart for inspection processing to be described later. Operation unit 70 can control operation of the inspection apparatus by using input from input unit 40, and output a status of each unit or an inspection result from output unit 50.

An inspection object position drive mechanism includes an actuator and a mechanism for fixing the inspection object, and moves the inspection object in accordance with an instruction from inspection object position control unit 80.

X-ray detector drive unit 22 includes orthogonal biaxial robot arm 22.1 and detector support unit 22.2 having an axis of rotation, and moves X-ray detector 23 to a designated position in accordance with an instruction from operation unit 70 through detector driving control unit 32. Detector driving control unit 32 transmits information about a position of X-ray detector 23 at that point in time to operation unit 70.

Operation unit 70 acquires a fluoroscopic X-ray image and transfers picked up image data at timing instructed by an instruction through detector driving control unit 32.

X-ray source 10 generates an electron beam from an electron gun 14 in accordance with an instruction from operation unit 70 through scanning X-ray source control mechanism 60, and converges the electron beam on a designated position on the target by electron beam convergence coil 13 and deflection yoke 12, to move X-ray focal point 17 at high speed. Accordingly, time for moving the focal point that can be electronically changed in position in scanning X-ray source 10 is negligibly short with reference to movement speed of and image pickup time for X-ray detector 23 and the inspection object position drive mechanism.

Figure 11:
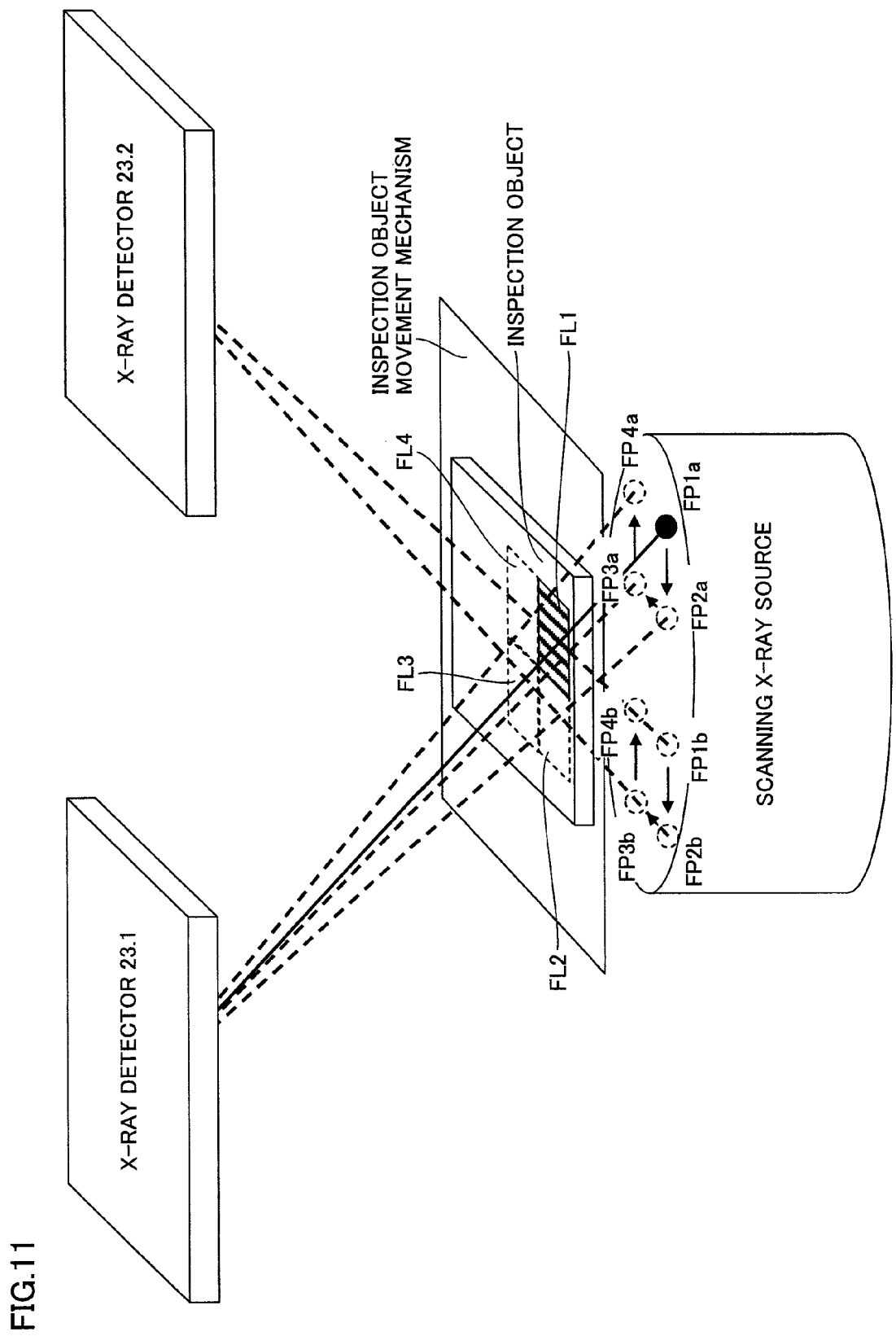
FIG. 11 is a conceptual diagram illustrating a case where transmitted X-ray images of four fields of view are successively picked up by the structure of the X-ray inspection apparatus shown in FIG. 10 according to one or more embodiments of the present invention.

FIG. 11 is a conceptual diagram illustrating a case where transmitted X-ray images of four fields of view are successively picked up by the structure of X-ray inspection apparatus 100 shown in FIG. 10.

Namely, FIG. 11 shows a structure where an inspection area in an inspection object is divided into four fields of view FL1 to FL4, and an enlarged image of each field of view is picked up with X-ray detectors 23.1 and 23.2. While the inspection area is divided into four fields of view in this case, it may be divided into any number more than one of fields of view.

An X-ray focal point position from which an X-ray is transmitted through field of view FL1 in an oblique direction to project field of view FL1 onto a large portion of X-ray detector 23.1 is set as a focal point FP1a. Stated another way, part of an X-ray generated with focal point FP1a as an originating point and transmitted through field of view 1 is projected onto X-ray detector 23.1, and two-dimensional distribution of its intensity is detected by X-ray detector 23.1. Similarly, X-ray focal points for projecting fields of view FL2 to FL4 onto a large portion of X-ray detector 23.1 are set as focal points FP2a to FP4a, and X-ray focal points for projecting fields of view FL1 to FL4 onto a large portion of X-ray detector 23.2 are set as focal points FP1b to FP4b, respectively.

First, scanning X-ray source 10 emits an X-ray from focal point FP1a, and X-ray detector 23.1 acquires a transmitted image of field of view FL1 from an oblique direction (obtains X-ray intensity distribution). Then, scanning X-ray source 10 emits an X-ray from focal point FP2a, and X-ray detector 23.1 acquires a transmitted image of field of view FL2 from an oblique direction. In this process, the transmitted X-ray images of fields of view FL1 and FL2 are picked up at a substantially identical angle, subjected to appropriate image processing, and can be used in the same manner to reconstruct an image for inspection. The same applies to image pickup with focal points FL3a and FL4a as well.

If a target position of the inspection object moved by the inspection object position movement mechanism during inspection has been set in advance, an incident angle of an X-ray to the X-ray detector during image pickup and the like can be stored in advance as a table based on relation of position between such focal point and the X-ray detector, to perform calculation for reconstruction based on the table.

Next, scanning X-ray source 10 irradiates the inspection object with an X-ray from focal point FP1b, and X-ray detector 23.2 acquires a transmitted image of field of view FL1 from an oblique direction. This irradiation angle is significantly different from that during image pickup with X-ray detector 23.1 described above. Accordingly, a resultant image can be effectively utilized as an image from a different angle for reconstructing an inspection image of field of view FL1. The same applies to focal points FP2b to FP4b as well.

Figure 12:
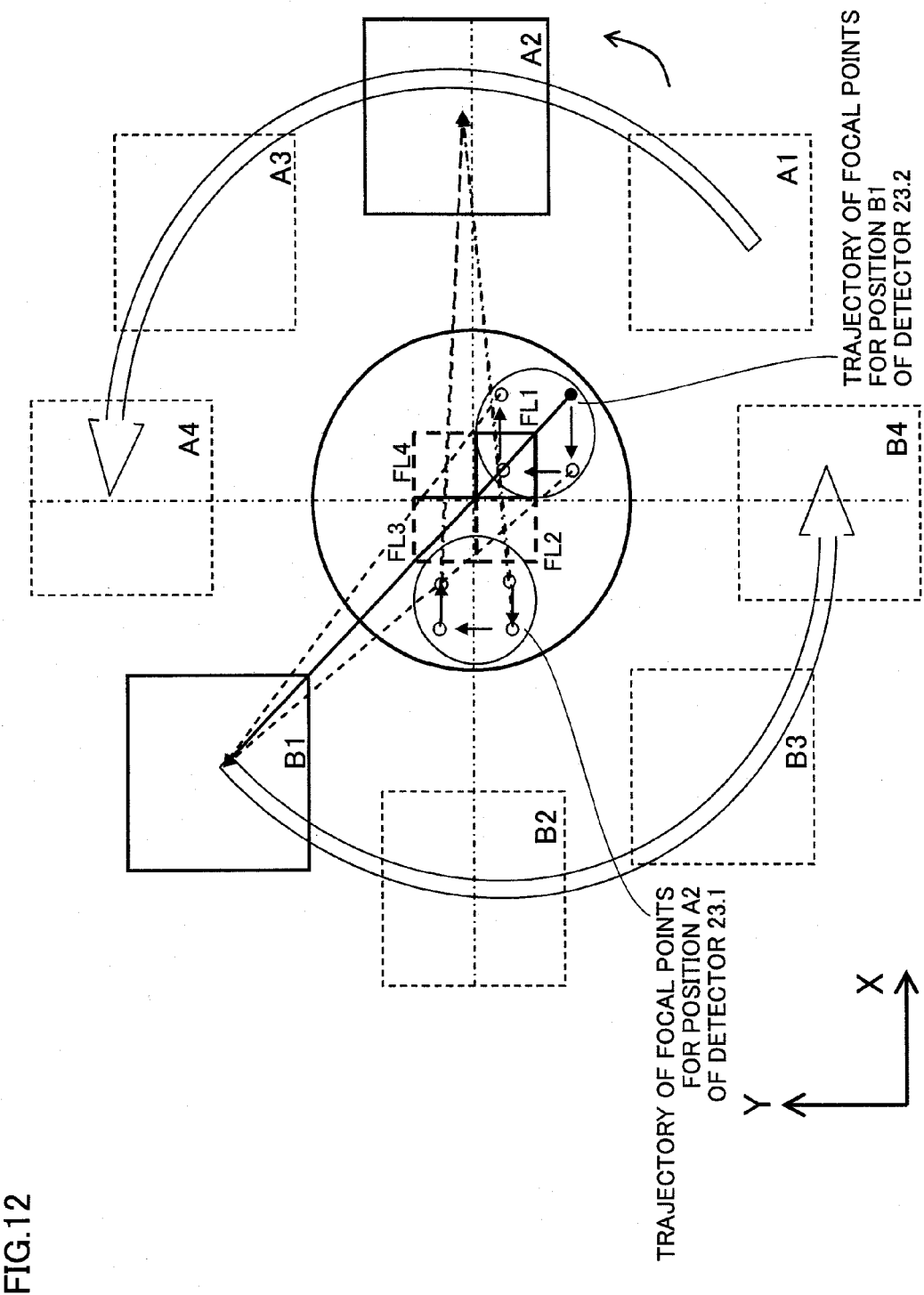
FIG. 12 shows arrangement of X-ray detectors and an inspection object shown in FIG. 11, when viewed from above the X-ray inspection apparatus according to one or more embodiments of the present invention.

FIG. 12 shows arrangement of the X-ray detectors and the inspection object shown in FIG. 11, when viewed from above X-ray inspection apparatus 100.

FIG. 12 shows an operation example on the assumption that eight transmitted X-ray images are equiangularly picked up. More or less than eight transmitted X-ray images may be picked up for reconstruction of one field of view. While images of the fields of view are picked up in the order of field of view FL1→field of view FL2→field of view FL3→field of view FL4 in the figure, the order of image pickup may be different from this one, or may be changed during image pickup. In addition, the order of positions of movement of X-ray detector 23 may be other than the illustrated order (A1→A2→A3→A4 and B1→B2→B3→B4). When performing image reconstruction with an iterative method while picking up images, by arranging the detectors in positions symmetrical with respect to a central point of a field of view as shown in the figure (e.g., A1→A2) to successively pick up images, reconstruction processing can be performed based on information about images picked up from different angles. Consequently, an image effectively contributing to calculation convergence can be obtained.

An image pickup sequence is generally described below.

X-ray detector 23.1 and X-ray detector 23.2 operate independently of each other in different ranges. Positions A1 and B1 of the X-ray detectors are initial positions of X-ray detectors 23.1 and 23.2, respectively. Positions A1 to A4 and positions B1 to B4 are positions of X-ray detectors 23.1 and 23.2, respectively, for acquiring transmitted images required for image reconstruction.

In the example shown in FIG. 12, X-ray detectors 23.1 and 23.2 move at a constant distance around the origin point of the image pickup system. Accordingly, when the image pickup system is viewed from above, each has a semicircular trajectory.

Four points enclosed with a circle of "trajectory of focal points for position A2 of detector 23.1" in FIG. 12 are X-ray focal point positions on the X-ray target during a period when detector 23.1 rests in position A2, which are the positions for picking up images of fields of view FL1 to FL4 with X-ray detector 23.1, as described with reference to FIG. 11. The same applies to a "trajectory of focal points for position B1 of detector 23.2" as well.

X-ray detector 23.1 moves from position A1 to A4 and X-ray detector 23.2 moves from position B1 to B4, while resting in each position to pick up an image. While one of X-ray detectors 23.1 and 23.2 picks up an image, the other operates to move to the next image pickup position.

The operation example shown in FIG. 12 where X-ray detector 23 does not rotate is suitable for an iterative reconstruction method and a tomosynthesis reconstruction method. This is because an iterative reconstruction method and tomosynthesis allow reconstruction regardless of an orientation of an X-ray detector. In such operation, X-ray detector 23 does not need to rotate. Therefore, the X-ray detector drive mechanism can be simplified, and speed and maintainability of the mechanism can be improved.

On the other hand, to operate the detector in a manner suitable for an analytical reconstruction method represented by the Feldkamp method, the detector may be caused to rotate to always face the same direction with respect to an inspection object while moving from one position to another.

Figure 13:
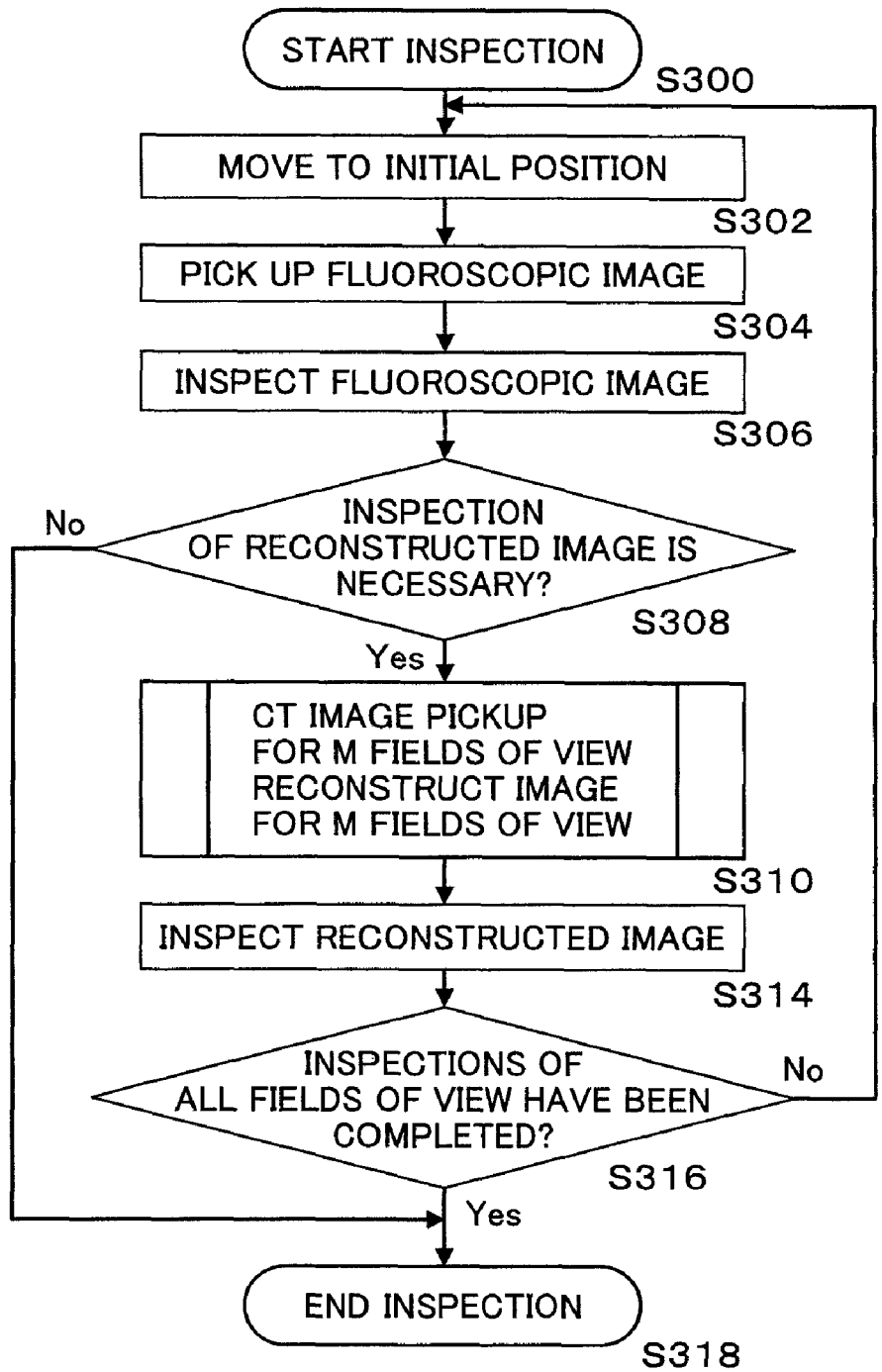
FIG. 13 is a flowchart of overall inspection of a reconstructed image by a movement mechanism shown in FIG. 10 according to one or more embodiments of the present invention.

FIG. 13 is a flowchart of overall inspection of a reconstructed image by the movement mechanism shown in FIG. 10.

Namely, when inspection is started (S300), X-ray inspection apparatus 100 moves X-ray detectors 23 and an inspection object to their initial positions (S302), and picks up a fluoroscopic image (S304). X-ray source 10 emits an X-ray to expose one of X-ray detectors 23. Although not particularly limited, X-ray detector 23.1 is moved to a position immediately above a field of view of the inspection object, for example, when such fluoroscopic image is picked up. Then, the X-ray emitted from X-ray source 10 passes through the field of view of the inspection object, and enters X-ray detector 23.1. Because an amount of absorbed X-ray varies with an X-ray transmission path, image data can be obtained from X-ray detector 23.1.

Then, it is determined whether or not the field of view of the inspection object (scope picked up in fluoroscopic image) is acceptable based on the acquired fluoroscopic image (S306). Because various methods for acceptance/rejection determination have been proposed and known, detailed description thereof will not be provided. For example, determination is made by binarizing the fluoroscopic image with a constant value, comparing the binarized fluoroscopic image with design information such as CAD data, and determining whether or not a component exists on the fluoroscopic image based on an area thereof.

Next, acceptance/rejection determination unit 78 of X-ray inspection apparatus 100 determines whether or not inspection with a reconstructed image is necessary (S308). A criterion for this determination may be set in advance based on design information such as CAD data, or may be determined based on a result of acceptance/rejection determination of the fluoroscopic image. For example, when a mounting board having components mounted only on one side thereof is inspected, acceptance/rejection determination with a reconstructed image may not be necessary because acceptance/rejection determination can be made with a fluoroscopic image.

If it is determined at step S308 that acceptance/rejection determination with a reconstructed image is necessary, X-ray inspection apparatus 100 performs CT image pickup for the M fields of view each time the positions of X-ray detectors 23.1 and 23.2 are moved while the position of the inspection object is fixed, and performs image reconstruction processing in parallel (S310).

Figure 30:
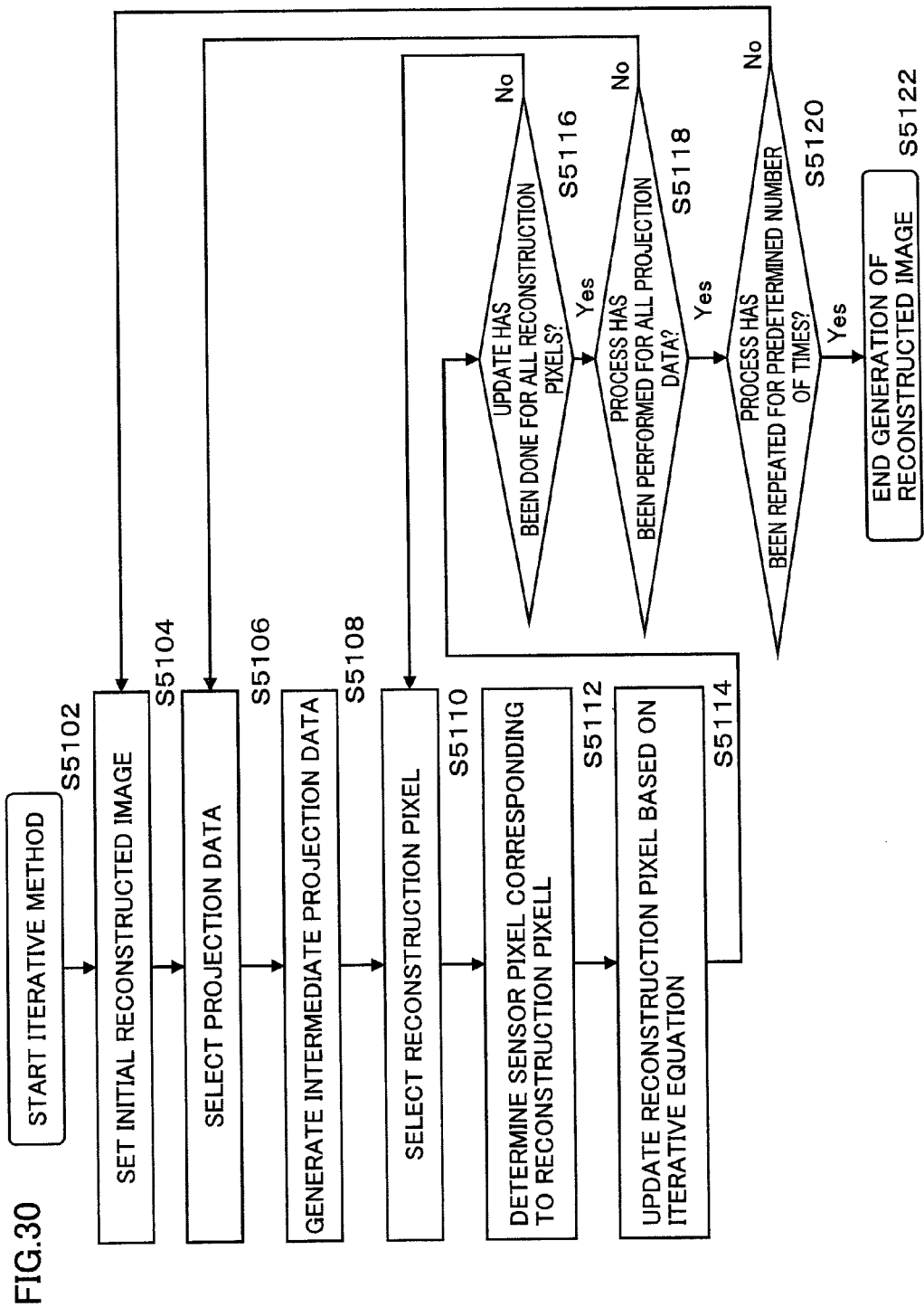
FIG. 30 is a flowchart illustrating the process with the iterative method according to one or more embodiments of the present invention.

When performing CT image pickup for the M fields of view, X-ray inspection apparatus 100 picks up images of the fields of view in the inspection object (reconstruction areas or areas similar to the scope picked up in the fluoroscopic image described above) from a plurality of directions. In parallel with this processing, X-ray inspection apparatus 100 performs processing for generating a reconstructed image from the images picked up from the plurality of directions. The reconstruction processing may be performed with an analytical method or an iterative method. With these methods, as described with reference to FIGS. 27 and 30, the reconstruction processing can be partially performed successively based on images picked up until that point in time, before a predetermined number of images are picked up.

The transmitted images picked up by X-ray inspection apparatus 100 are not equally spaced or equiangular.

Next, X-ray inspection apparatus 100 makes acceptance/rejection determination with the reconstructed image (S314). The acceptance/rejection determination may be made with a method of directly using three-dimensional data, a method of using two-dimensional data (tomographic image), or a method of using one-dimensional data (profile). Any of these known methods for acceptance/rejection determination that is suitable for an inspection item may be used. In exemplary acceptance/rejection determination, first, acceptance/rejection determination unit 78 binarizes a three-dimensional reconstructed image with a constant value. A position of a component in the reconstructed image is specified based on design information such as CAD data. A volume of a pixel adjacent to the position of the component is calculated based on the binarized image, to determine presence or absence of the component.

Next, operation unit 70 in X-ray inspection apparatus 100 determines whether or not inspections of all fields of view have been conducted (S316). The determination may be made by setting the number of fields of view to be inspected before inspection, and counting the number of fields of view that have been inspected with each inspection. If the determination shows that all fields of view have been inspected, the inspection ends (S318). If fields of view other than the M fields of view need to be inspected and all fields of view have not been inspected, the process returns to step S302, and X-ray inspection apparatus 100 conducts inspection of the next field of view.

In the image pickup sequence of X-ray inspection apparatus 100, time to move to the second and subsequent fields of view is reduced. This is because when the last image pickup for one field of view is started, the other X-ray detector is simultaneously moved to an image pickup position for the next field of view. Here, only an X-ray focal point position is changed in order to eliminate the need to move the inspection object movement mechanism such as the stage. Namely, as shown in the operation example, images are picked up at angles that vary with a field of view While such not equally-spaced image pickup may result in degradation in reconstructed image, the degradation can be reduced with an iterative method.

While inspection is conducted with both the fluoroscopic image and the reconstructed image in FIG. 13, inspection can be conducted only with the reconstructed image without using the fluoroscopic image. Because reconstruction processing usually takes relatively long time, by making acceptance/rejection determination with a fluoroscopic image before inspection with a reconstructed image, overall inspection time can be reduced.

Figure 14:
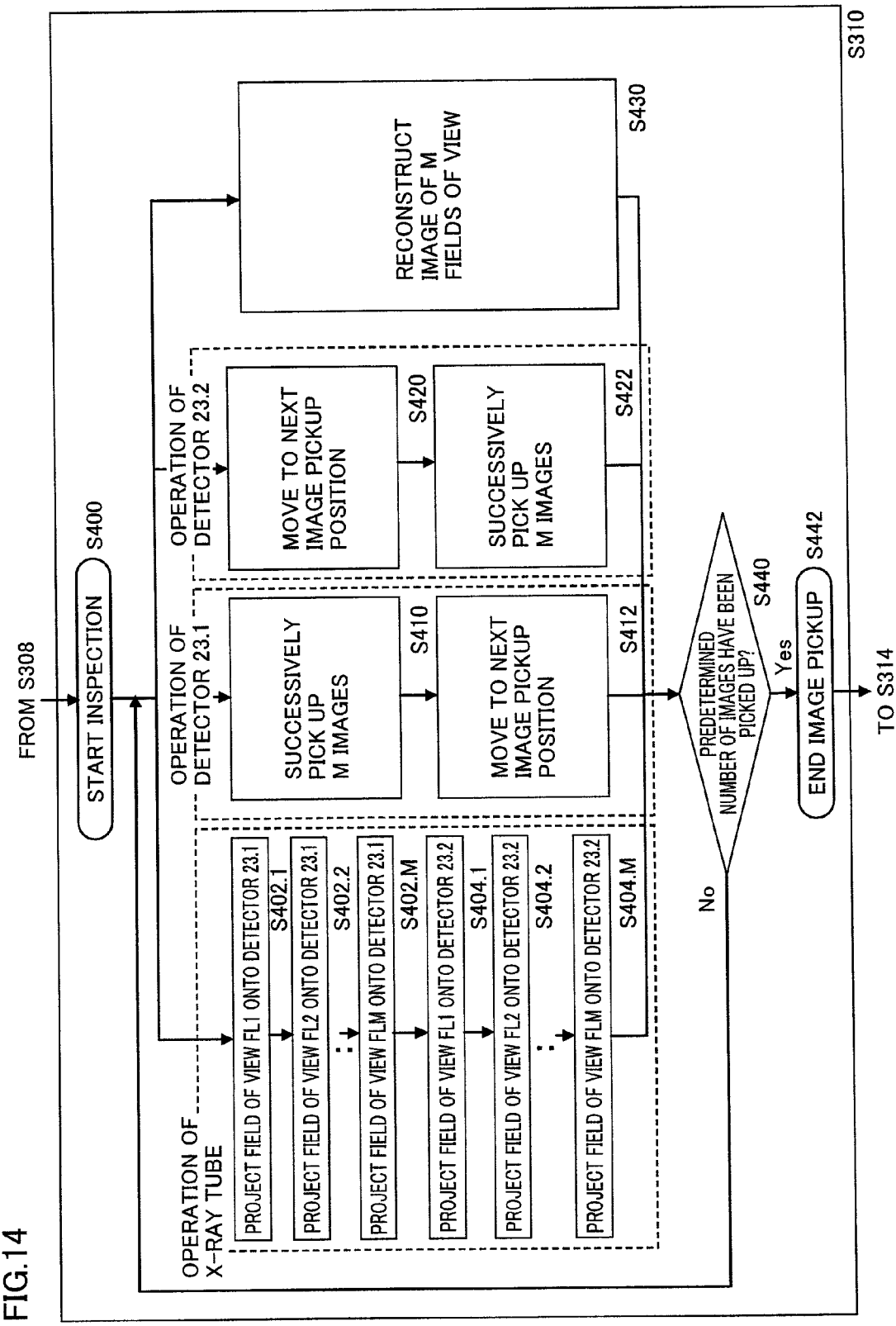
FIG. 14 is a flowchart illustrating in further detail a process of step 310 shown in FIG. 13 according to one or more embodiments of the present invention.

FIG. 14 is a flowchart illustrating in further detail the process of step 310 shown in FIG. 13.

Figure 15:
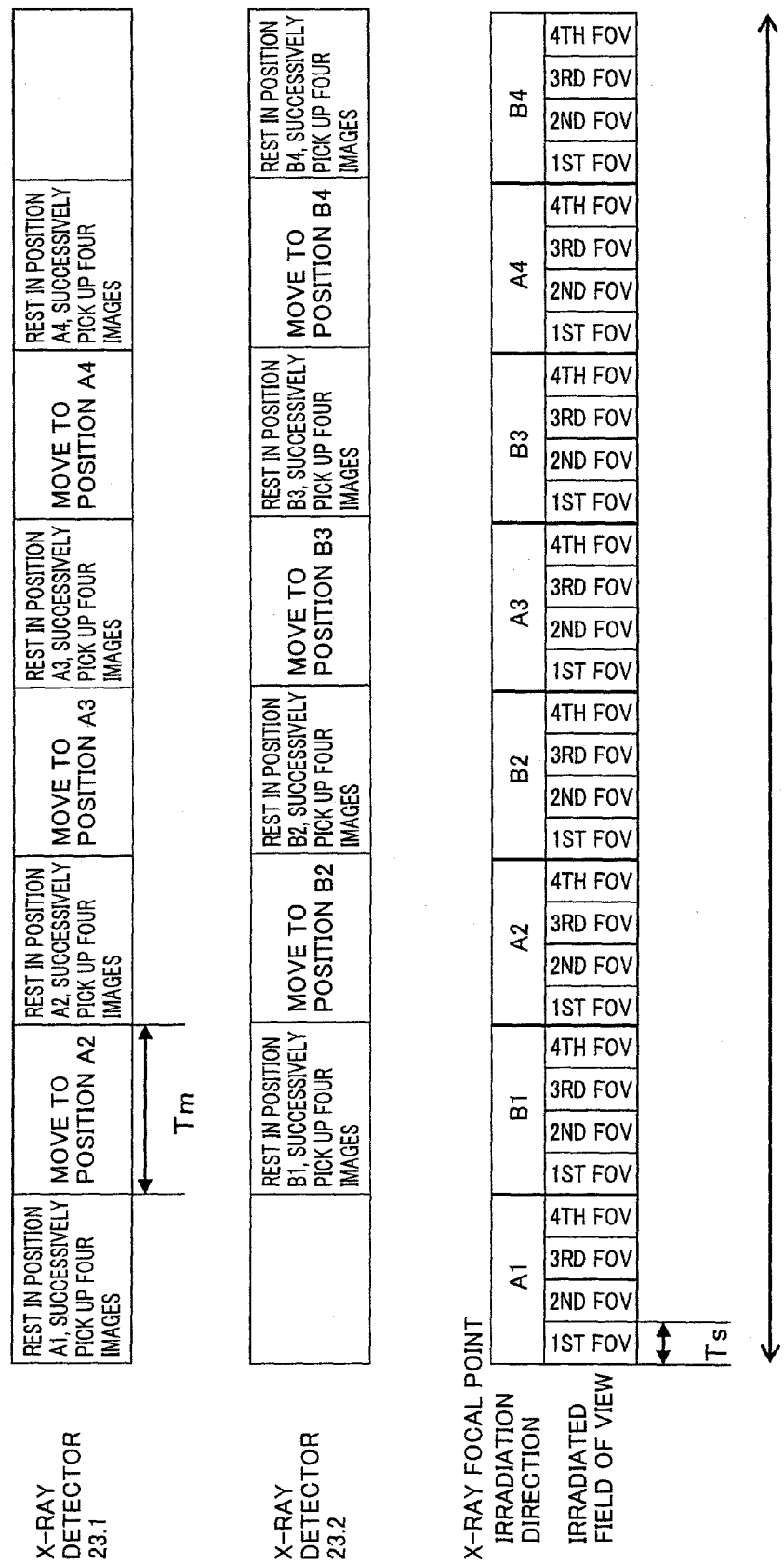
FIG. 15 is a timing chart illustrating relation between positions of X-ray detectors and fields of view which are objects of image pickup according to one or more embodiments of the present invention.

FIG. 15 is a timing chart illustrating relation between movement of X-ray detectors 23 and positions of X-ray detectors 23 for picking up images through X-ray irradiation from X-ray source 10, and fields of view which are objects of image pickup. In FIG. 15, operations of X-ray source 10, X-ray detector 23.1 and X-ray detector 23.2 are separately shown in a lateral direction. They operate with temporal coincidence in the lateral direction of the chart.

X-ray detector 23.1 and X-ray detector 23.2 successively pick up images of the M fields of view at timings not overlapping with each other. Data on picked up images can be transferred simultaneously with image pickup or position movement.

In FIG. 15, time for image pickup and time for detector movement are indicated as Ts and Tm, respectively. Picked up images can be transferred to operation unit 70 simultaneously with image acquisition or position movement of X-ray detectors 23.

Assuming that eight transmitted images need to be picked up for image reconstruction with the image pickup method of X-ray inspection apparatus 100, time required for acquiring the necessary eight images for reconstruction in the operation example of FIG. 15 is expressed as 32Ts if $4Ts \geq Tm$ is satisfied, and expressed as 8Ts+6Tm if $4Ts<Tm$ is satisfied. In either case, time required for picking up images of four fields of view from eight directions is substantially reduced from that with the conventional method (32Ts+31Tm).

Referring to FIGS. 14 and 15, when the image pickup process is started (S400), X-ray inspection apparatus 100 transmits X-rays from X-ray source 10 through M fields of view FL1 to FLM to successively project them onto X-ray detector 23.1 (S402.1 to S402.M), and X-ray detector 23.1 (in position A1, for example) successively picks up M images of each of the M fields of view (S410).

In X-ray inspection apparatus 100, while X-ray detector 23.1 picks up images of the X-rays from X-ray source 10, X-ray detector 23.2 moves to the next image pickup position (position B1, for example) (S420).

Next, X-rays are generated from X-ray focal point position FP1b, and transmitted through M fields of view FL1 to FLM to be successively projected onto X-ray detector 23.2 (S404.1 to S404.M), and X-ray detector 23.2 (in position B1, for example) successively picks up M images of each of the M fields of view (S422). While X-ray detector 23.2 picks up images, X-ray detector 23.1 moves to the next predetermined image pickup position (position A2, for example) (S412).

When the image pickup by X-ray detector 23.2 (in position B1, for example) and the movement of X-ray detector 23.1 are completed, operation unit 70 determines whether or not a predetermined number of images have been picked up (S440). If the images have been picked up, the process ends (S422), and returns to step S314.

If the predetermined number of images have not been picked up, X-ray inspection apparatus 100 immediately moves the X-ray focal point position to a position corresponding to the next image pickup by X-ray detector 23.1, and X-ray detector 23.1 (in position A2, for example) successively picks up M images for each of the M fields of view (S410). During this image pickup, X-ray detector 23.2 moves to the next predetermined image pickup position (position B2, for example) (S422).

In parallel with the image pickup by X-ray detector 23 and the movement of X-ray detector 23, image reconstruction processing for the M fields of view is performed (S430). This will be described later.

By repeating such processing, the number of images required for image reconstruction can be obtained while reducing downtime of the X-ray source due to the time for movement of the X-ray detector.

While the image reconstruction processing is performed in parallel with the image pickup for the M fields of view in the flowchart of FIG. 14, image reconstruction can alternatively be performed collectively after the predetermined number of images have been picked up.

Figure 16:
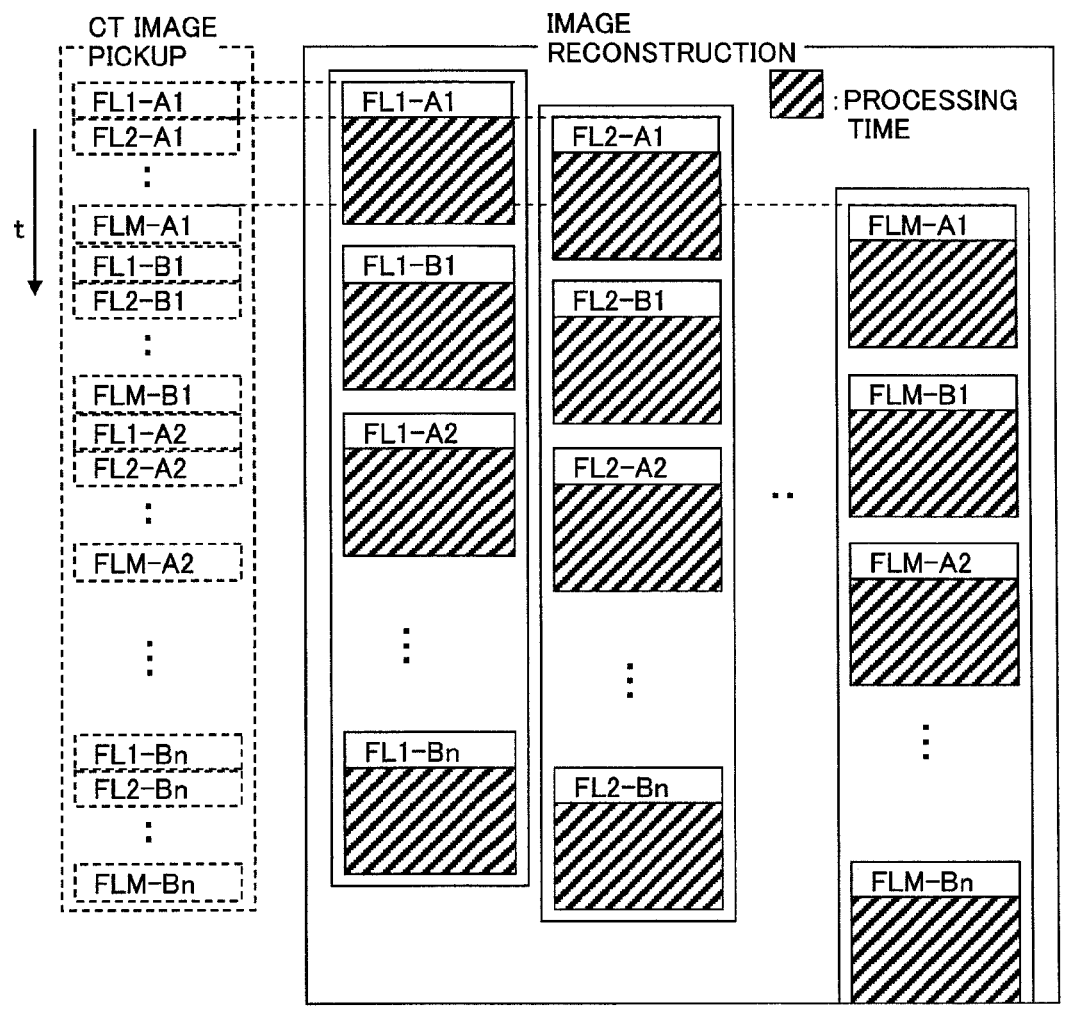
FIG. 16 is a timing chart illustrating time course of CT image pickup and an image reconstruction process according to one or more embodiments of the present invention.

FIG. 16 is a timing chart illustrating time course of the CT image pickup and the image reconstruction processing in the flowchart of FIG. 14.

Namely, FIG. 16 illustrates steps of image reconstruction for the process of "reconstruct image of M fields of view" at step S430 in FIG. 14.

In FIG. 16, a symbol "FL1-A1" means a "transmitted image of field of view FL1 picked up in detector position A1." The same applies to the other numbers of fields of view FLm (m=1, . . . M) and the other signs of detectors (Ai, Bi: i=1, 2, . . . n) as well. While transmitted images from 2 (=number of detectors)×n directions are used in the example of FIG. 16, more or less than two detectors may be used.

The transmitted X-ray images of fields of view FL1 to FLM obtained by the image pickup steps at steps S410 and S422 in FIG. 14 are acquired through an image pickup process in all detector positions, such that M transmitted images corresponding to detector position A1 are acquired, and then M transmitted images corresponding to detector position B1 are acquired, as shown within a dotted frame indicated with "CT image pickup" in FIG. 16.

In order to reconstruct an image of one field of view, transmitted images from a plurality of angles corresponding to that field of view need to be successively processed with an image reconstruction algorithm. For this reason, by performing image processing corresponding to each field of view in parallel, a reconstructed image for each field of view is obtained.

Figure 27:
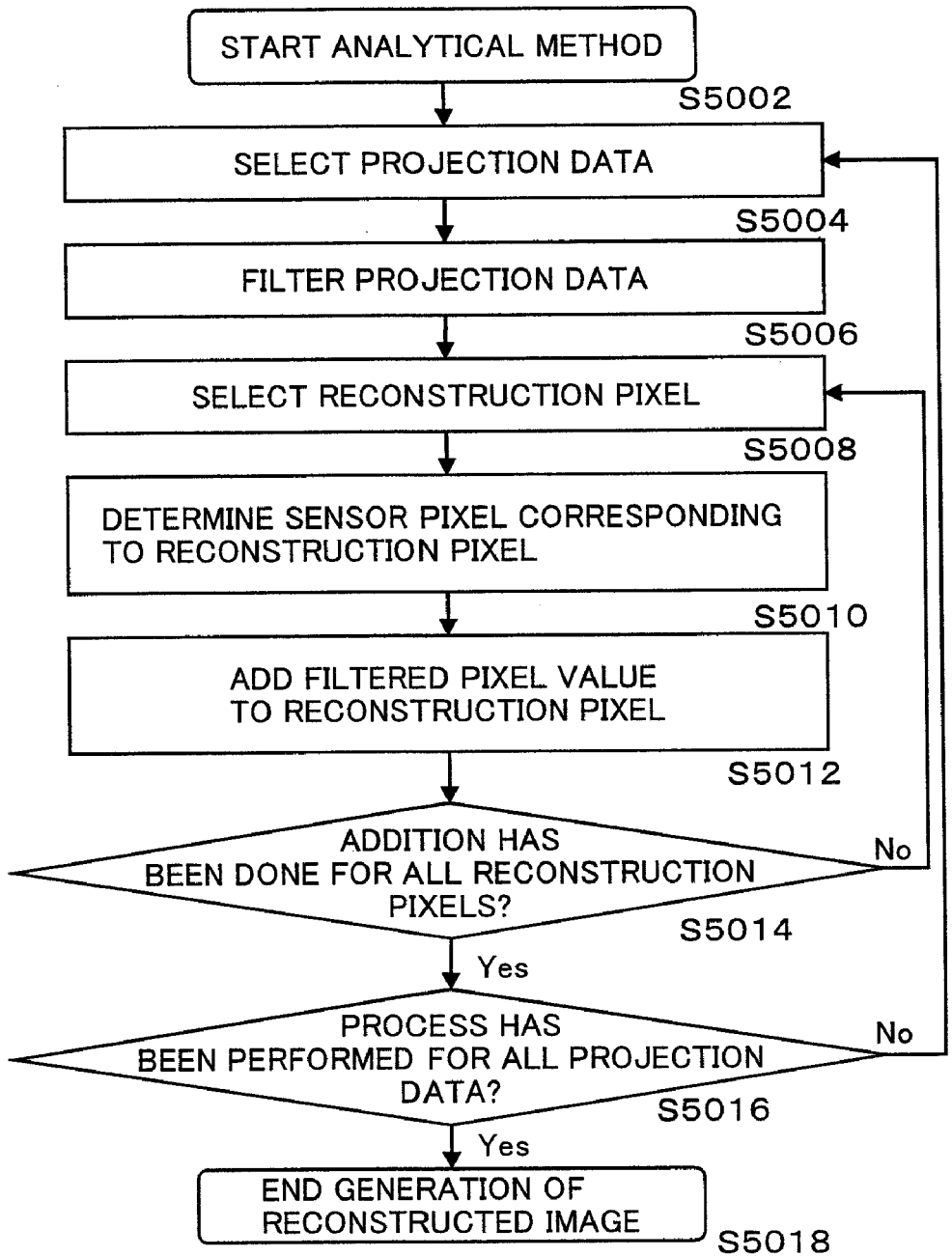
FIG. 27 is a flowchart showing process steps of a filtered back-projection method according to one or more embodiments of the present invention.
Figure 28:
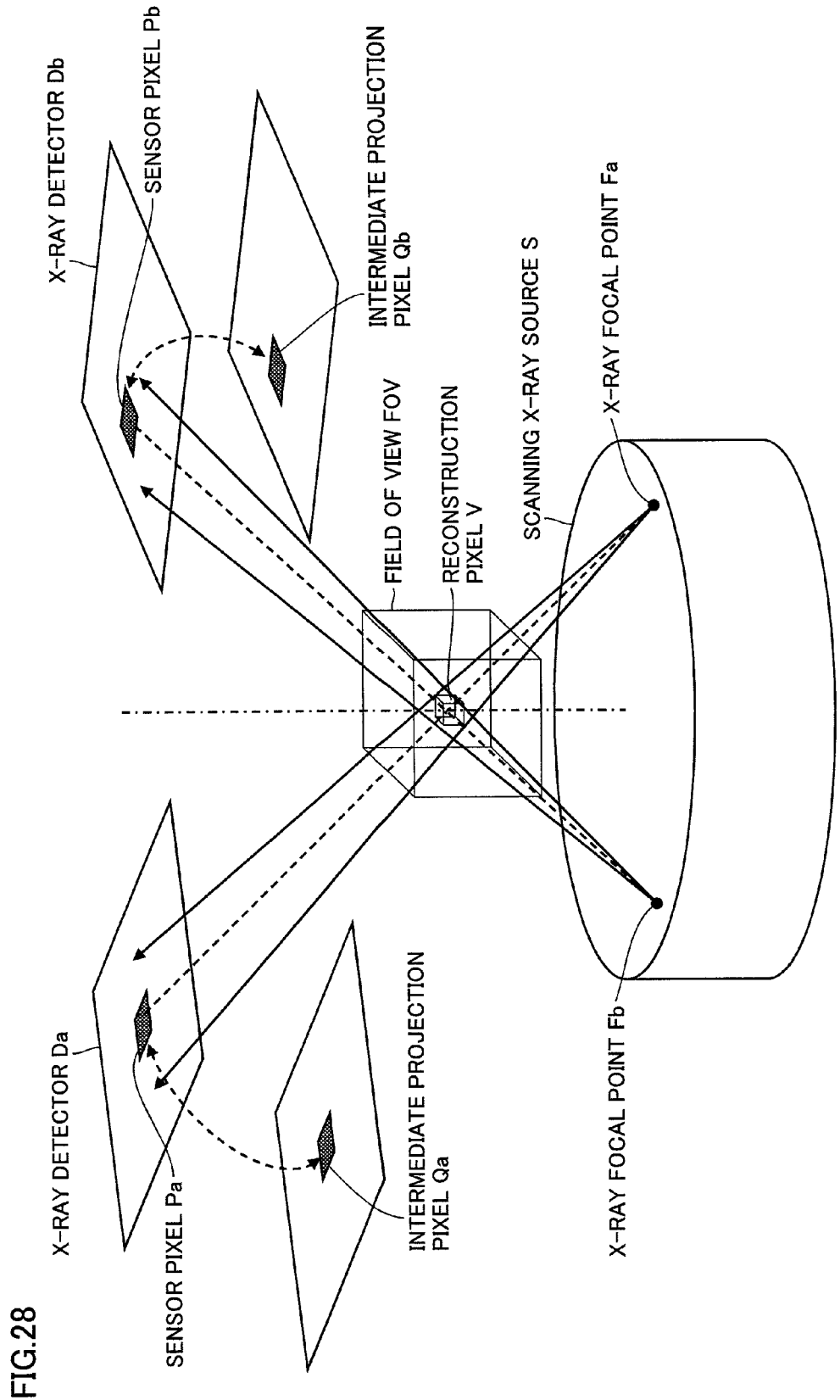
FIG. 28 is a conceptual diagram showing a concept of a process with an iterative method, when a scanning X-ray source is used according to one or more embodiments of the present invention.
Figure 29:
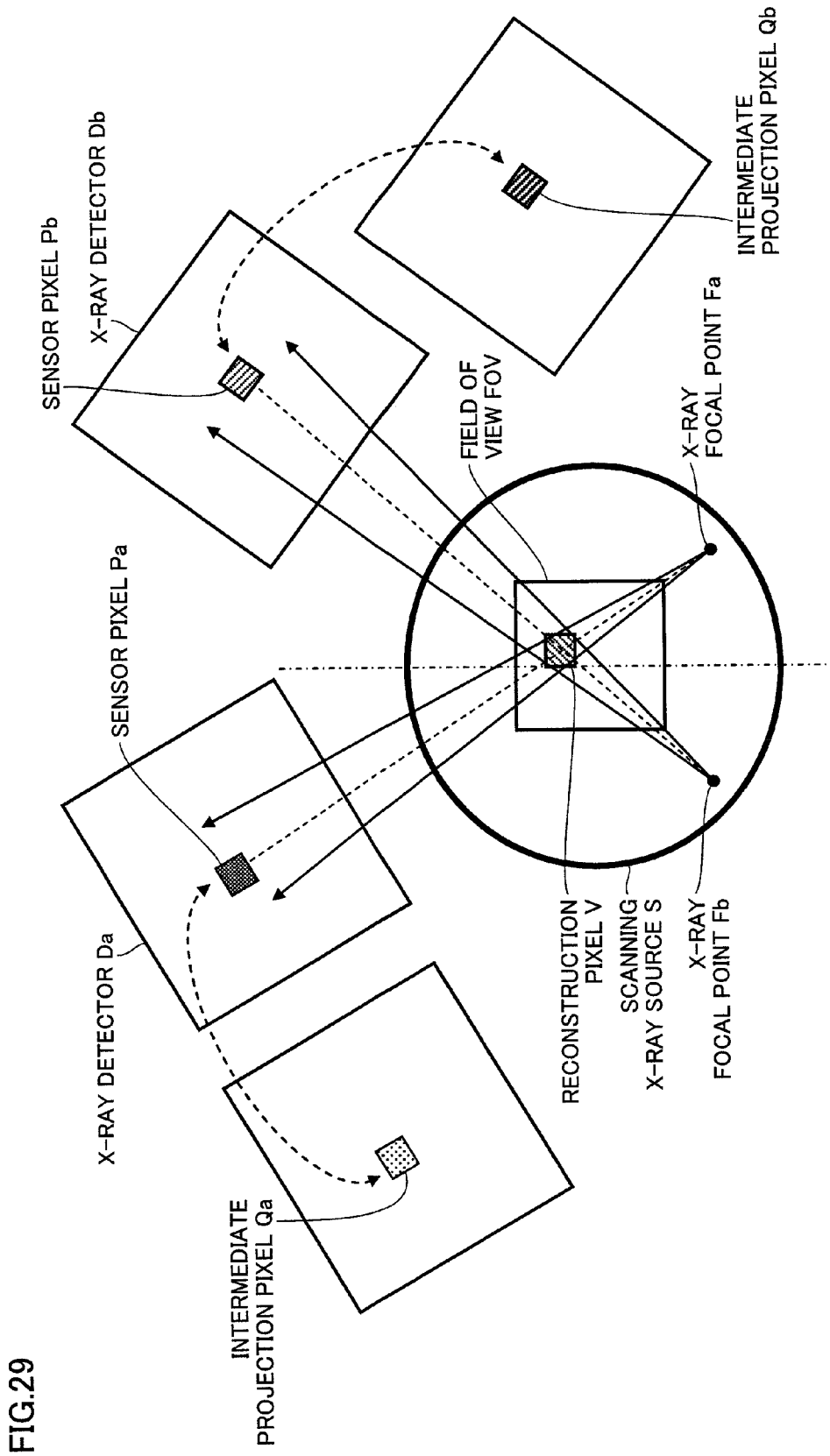
FIG. 29 is a top view of the conceptual diagram of FIG. 28 according to one or more embodiments of the present invention.

Namely, with the analytical method, a process of successively adding filtered pixel values is essentially performed, as shown in FIG. 27, and thus reconstruction processing can be partially performed even if a predetermined number of images have not been picked up. With the iterative method of successively updating an initial projection image, this operation can also be performed each time a partial transmitted image is obtained.

While such image reconstruction processing can of course be performed after all of a predetermined number of transmitted images for a field of view are obtained, inspection time can be effectively utilized by inputting one transmitted image to the reconstruction algorithm upon acquiring the image, and performing reconstruction processing while picking up a transmitted image of another field of view, as shown in FIG. 16.

Here, three-dimensional position information about an X-ray focal point, a field of view, and a detector for an obtained transmitted image is associated with the transmitted image, and input to the reconstruction algorithm. This position information may be determined with a predetermined pattern, stored, and input. Alternatively, by detecting positions of an X-ray focal point, a field of view, and a detector during image pickup, and inputting deviation from predetermined positions as correction amounts, a reconstructed image of higher image quality can be obtained. Methods for detecting those positions are well known, and are thus not described in detail.

Modification of First Embodiment

Figure 17:
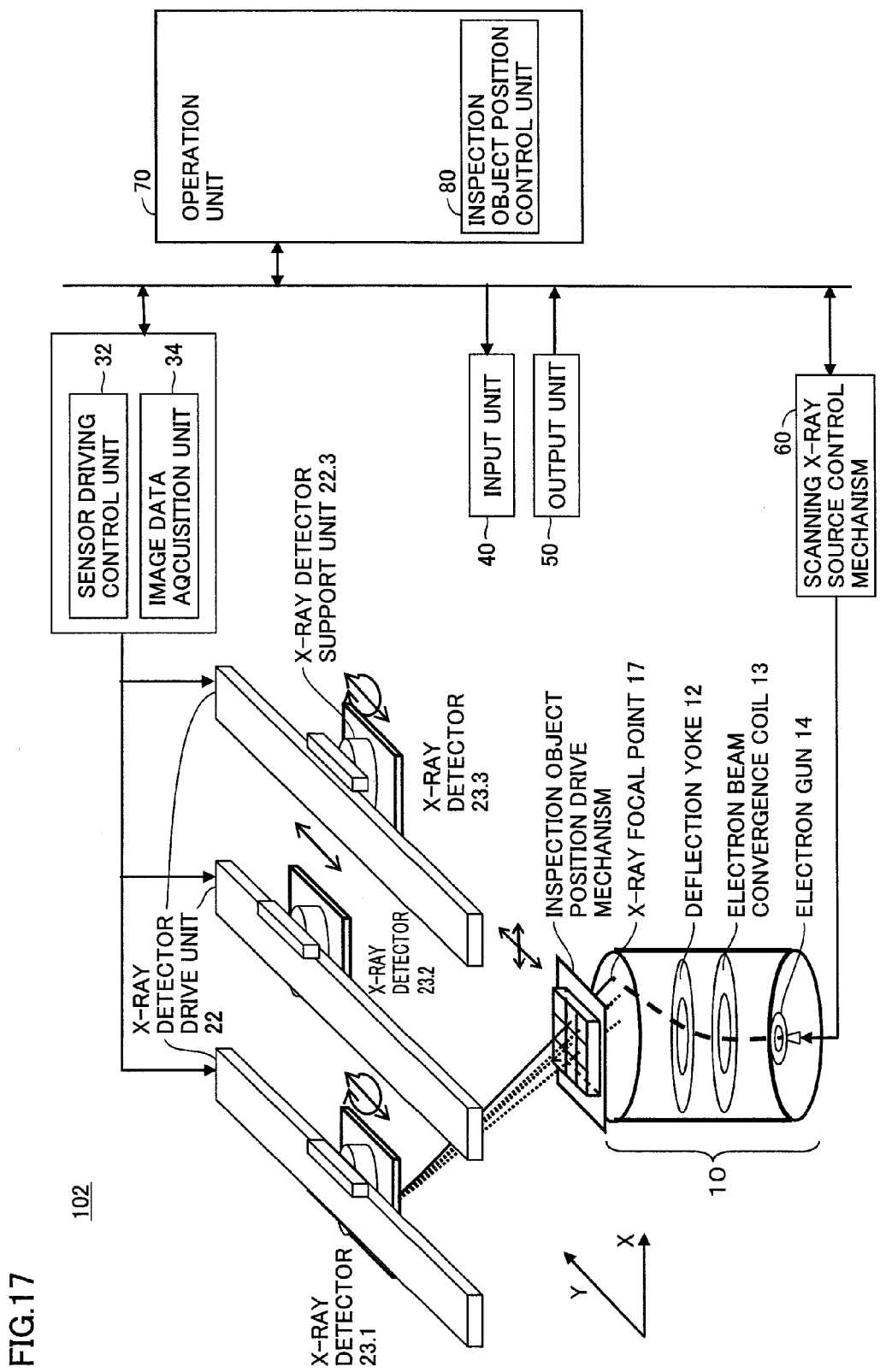
FIG. 17 illustrates a structure of an X-ray inspection apparatus in a modification of the first embodiment.

FIG. 17 illustrates a structure of an X-ray inspection apparatus 102 in a modification of the first embodiment. X-ray inspection apparatus 102 uses rectilinearly moving X-ray detectors, and a scanning X-ray source as X-ray source 10. The structural and operational difference between X-ray inspection apparatus 100 in the first embodiment and X-ray inspection apparatus 102 in the modification of the first embodiment is basically that X-ray inspection apparatus 102 includes three X-ray detectors 23 and operates in a different manner.

Namely, in X-ray inspection apparatus 102, three X-ray detectors 23.1, 23.2 and 23.3 are capable of Y movement and θ rotation independently of one another. FIG. 17 shows an operation mechanism of X-ray detector drive unit 22 in which an X-ray detector support unit 22.3 is rotatable and movable on a rail in the Y direction. Any mechanism other than that shown in FIG. 17 may be used as long as it has similar functions. Further, the rotation mechanism of X-ray detector 23 is not always necessary depending on a reconstruction method.

The scanning X-ray source as X-ray source 10 can move an X-ray focal point position to an arbitrary position on the X-ray target at high speed.

The same parts as those in FIGS. 1 and 10 are denoted by the same reference characters. Again in FIG. 17, portions necessary for description are extracted and illustrated from portions directly related to control of an X-ray focal point position, control of an X-ray detector position, control of an inspection object position, and the like.

While three independently movable X-ray detectors are used in FIG. 17, two or more X-ray detectors may be used. Because the use of an odd number of X-ray detectors has an advantage described below, it is desirable to provide three or more odd number of X-ray detectors. Namely, by providing an odd number of X-ray detectors, an X-ray detector moving on a middle rail can pick up an image of an inspection object from directly above the object. This is suitable for picking up the fluoroscopic image at step S304 in the operation in accordance with the flowchart illustrated in FIG. 13, for example. From the viewpoint of minimizing the number of detectors and the number of movement mechanisms, it is desirable to provide three detectors in terms of cost.

In the structure shown in FIG. 17, X-ray detector drive unit 22 includes detector support unit 22.3 capable of moving an X-ray detector on a rail in the Y direction and capable of rotating about the axis of rotation, and moves and rotates X-ray detector 23.

As in the structure shown in FIG. 10, a field of view of an inspection object is capable of X-Y movement independently of X-ray detectors 23.1, 23.2 and 23.3 described above, by the inspection object position drive mechanism (X-Y stage having the inspection object placed thereon or the like) controlled by inspection object position control unit 80 in operation unit 70. Further, as described above, the scanning X-ray source as X-ray source 10 can move X-ray focal point position 17 to an arbitrary position on the X-ray target at high speed.

Operation unit 70 transmits instructions to detector driving control unit 32, image data acquisition unit (X-ray detector controller) 34, and scanning X-ray source control mechanism 60, and executes a program illustrated in a flowchart for inspection processing to be described later. Operation unit 70 can also control operation of the inspection apparatus in accordance with input from input unit 40, and output a status of each unit or an inspection result from output unit 50.

The inspection object position drive mechanism includes an actuator and a mechanism for fixing the inspection object, and moves the inspection object in accordance with an instruction from inspection object position control unit 80.

X-ray detector drive unit 22 moves X-ray detector 23 to a designated position in accordance with an instruction from operation unit 70 through detector driving control unit 32. Detector driving control unit 32 transmits information about a position of X-ray detector 23 at that point in time to operation unit 70.

Operation unit 70 acquires a fluoroscopic X-ray image and transfers picked up image data at timing instructed by an instruction through detector driving control unit 32.

X-ray source 10 generates an electron beam in accordance with an instruction from operation unit 70 through scanning X-ray source control mechanism 60, and converges the electron beam on a designated position on the target by electron beam convergence coil 13 and deflection yoke 12, to move X-ray focal point 17 at high speed.

Figure 18:
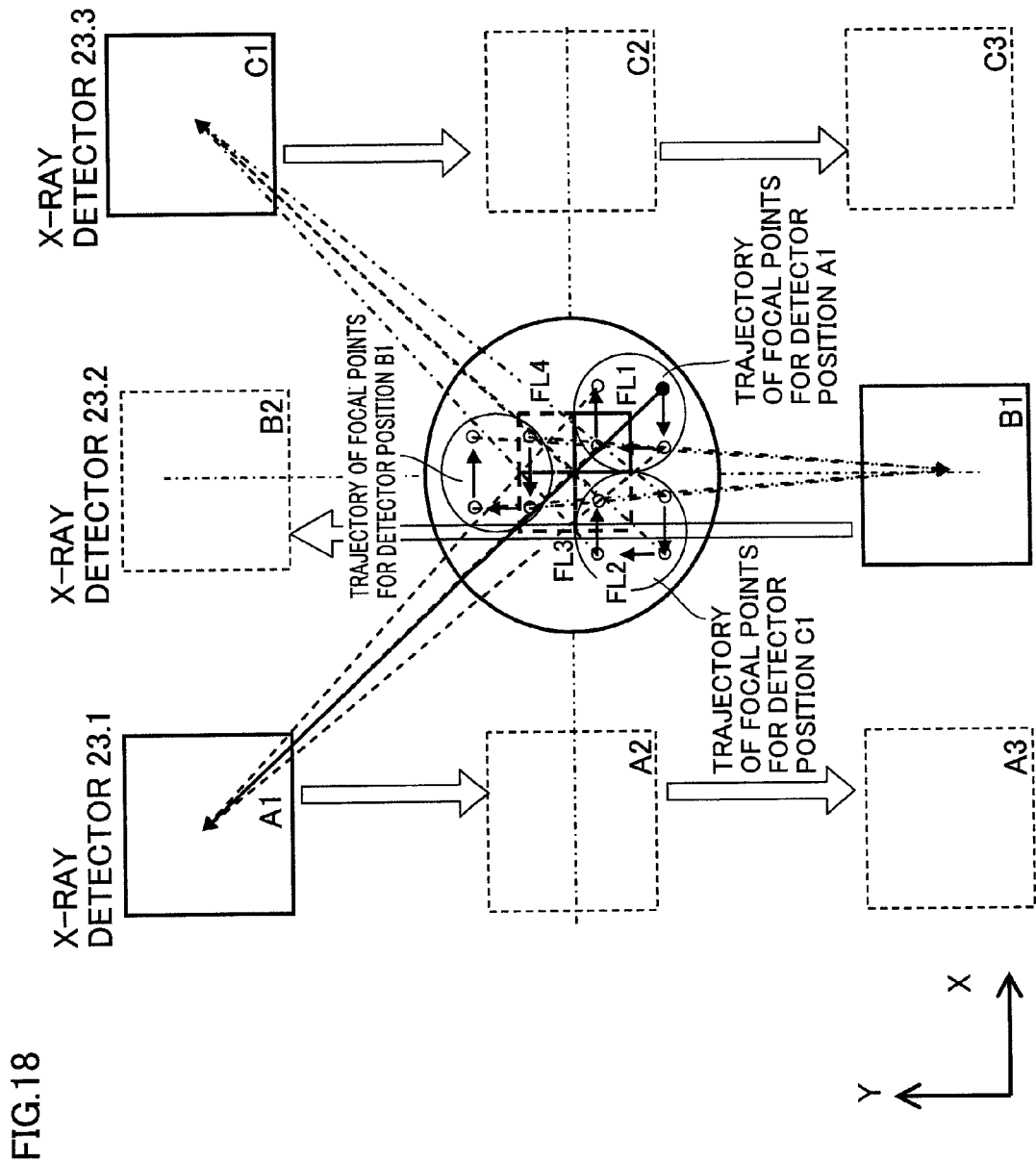
FIG. 18 is a top view showing movement trajectories of X-ray detectors and a running X-ray source in the structure of the X-ray inspection apparatus according to one or more embodiments of the present invention.

FIG. 18 is a top view showing movement trajectories of X-ray detectors 23 and the running X-ray source in the structure of X-ray inspection apparatus 102 shown in FIG. 17.

FIG. 18 shows an operation example in the structure of FIG. 17, when viewed from above. In this operation example, it is assumed that three fluoroscopic X-ray images of each of four fields of view, namely, 3×4=12 fluoroscopic X-ray images are picked up from different angles by scanning an X-ray focal point position, with X-ray detector 23.1 fixed in position A1, X-ray detector 23.2 fixed in position B1, and X-ray detector 23.3 fixed in position C1 as image pickup positions of X-ray detectors 23.

In FIG. 18, as described above, each of X-ray detectors 23.1, 23.2 and 23.3 has a mechanism capable of rectilinearly moving on a rail. In addition, each of X-ray detectors 23.1, 23.2 and 23.3 has a rotation mechanism capable of rotating about the center of the X-ray detector as necessary.

In FIG. 18, positions A1 to A3, B1 to B2, and C1 to C3 are positions of X-ray detectors 23.1, 23.2, and 23.3 for acquiring fluoroscopic images required for image reconstruction, respectively. The numbers 1 to 3 appended to the positions indicate the order of image pickup. X-ray detector 23.1 initially picks up images in position A1, and lastly picks up images in position A3. X-ray detector 23.2 initially picks up images in position B1, and lastly picks up images in position B2. X-ray detector 23.3 initially picks up images in position C1, and lastly picks up images in position C3.

The operation example in FIG. 18 is suitable for reconstruction processing with the iterative method. When the analytical method represented by the Feldkamp method is used, it is preferable that X-ray detector 23 rotates such that a direction of X-ray irradiation and a direction of X-ray detector 23 are controlled to be identical to each other in each image pickup position. Namely, in the analytical method in which projection data is usually filtered, a desirable filtering direction is perpendicular to a direction of an X-ray transmission path. Therefore, when the analytical method is used, it is preferable to pick up an image with an X-ray detector arranged perpendicularly to the X-ray transmission path, namely, with an X-ray detector directed to a field of view.

Figure 19:
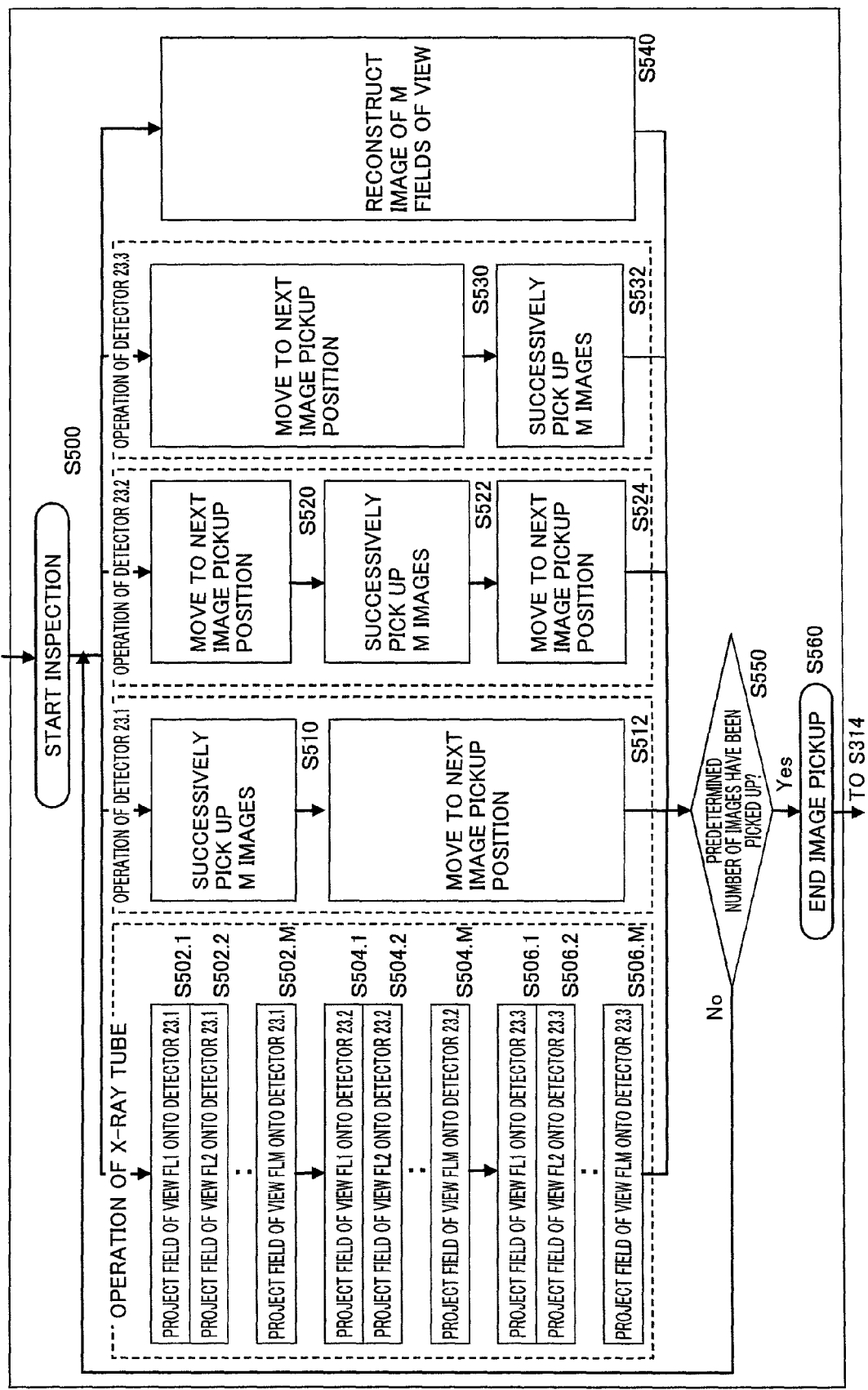
FIG. 19 is a flowchart illustrating in further detail the operation of the process of step 310 shown in FIG. 13 in the modification of the first embodiment.

FIG. 19 is a flowchart illustrating in further detail the operation of the process of step 310 shown in FIG. 13 in the modification of the first embodiment.

Referring to FIG. 19, when the image pickup process is started (S500), X-ray inspection apparatus 102 transmits X-rays from X-ray source 10 through M fields of view FL1 to FLM to successively project them onto X-ray detector 23.1 (S502.1 to S502.M), and X-ray detector 23.1 (in position A1, for example) successively picks up M images of each of the M fields of view (S510).

In X-ray inspection apparatus 102, while X-ray detector 23.1 picks up images of the X-rays from X-ray source 10, X-ray detector 23.2 and X-ray detector 23.3 move to the next image pickup positions (positions B1 and C1, for example) (S520, S530).

Next, X-rays are generated from a X-ray focal point position corresponding to X-ray detector 23.2, and transmitted through M fields of view FL1 to FLM to be successively projected onto X-ray detector 23.2 (S504.1 to S504.M), and X-ray detector 23.2 (in position B1, for example) successively picks up M images of each of the M fields of view (S522). While X-ray detector 23.2 picks up images, X-ray detector 23.1 and X-ray detector 23.3 move to the next predetermined image pickup positions (positions A2 and C1, for example) (S51, S532).

When the image pickup by X-ray detector 23.2 (in position B1, for example) and the movement of X-ray detector 23.1 and X-ray detector 23.3 are completed, X-rays are generated from an X-ray focal point position corresponding to X-ray detector 23.3, and transmitted through M fields of view FL1 to FLM to be successively projected onto X-ray detector 23.3 (S506.1 to S506.M), and X-ray detector 23.3 (in position C1, for example) successively picks up M images for each of the M fields of view (S532).

When the image pickup by X-ray detector 23.3 (in position C1, for example) and the movement of X-ray detector 23.1 and X-ray detector 23.2 are completed, operation unit 70 determines whether or not a predetermined number of images have been picked up (S550). If the images have been picked up, the process ends (S560), and returns to step S314.

If the predetermined number of images have not been picked up, X-ray inspection apparatus 102 immediately moves the X-ray focal point position to a position corresponding to the next image pickup by X-ray detector 23.1, and X-ray detector 23.1 (in position A2, for example) successively picks up M images for each of the M fields of view (S510).

As described above, each of X-ray detectors 23.1, 23.2 and 23.3 picks up images during movement of the other X-ray detectors.

In parallel with the image pickup by X-ray detector 23 and the movement of X-ray detector 23, image reconstruction processing for the M fields of view is performed (S540).

By repeating such processing, the number of images required for image reconstruction can be obtained while reducing downtime of the X-ray source due to the time for movement of the X-ray detector.

While the image reconstruction processing is performed in parallel with the image pickup for the M fields of view in the flowchart of FIG. 19, image reconstruction can alternatively be performed collectively after the predetermined number of images have been picked up.

Figure 20:
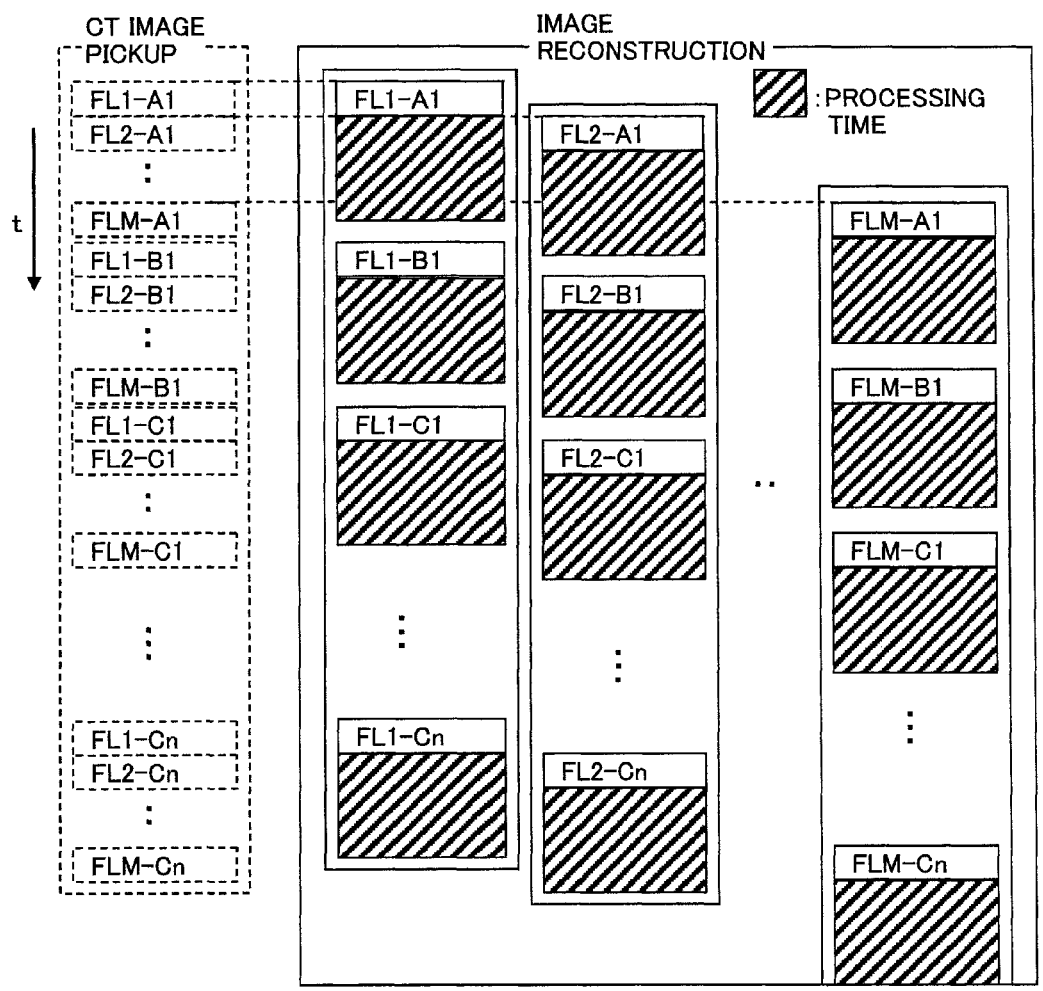
FIG. 20 is a timing chart illustrating time course of CT image pickup and an image reconstruction process in the flowchart of FIG. 19 according to one or more embodiments of the present invention.
Figure 21:
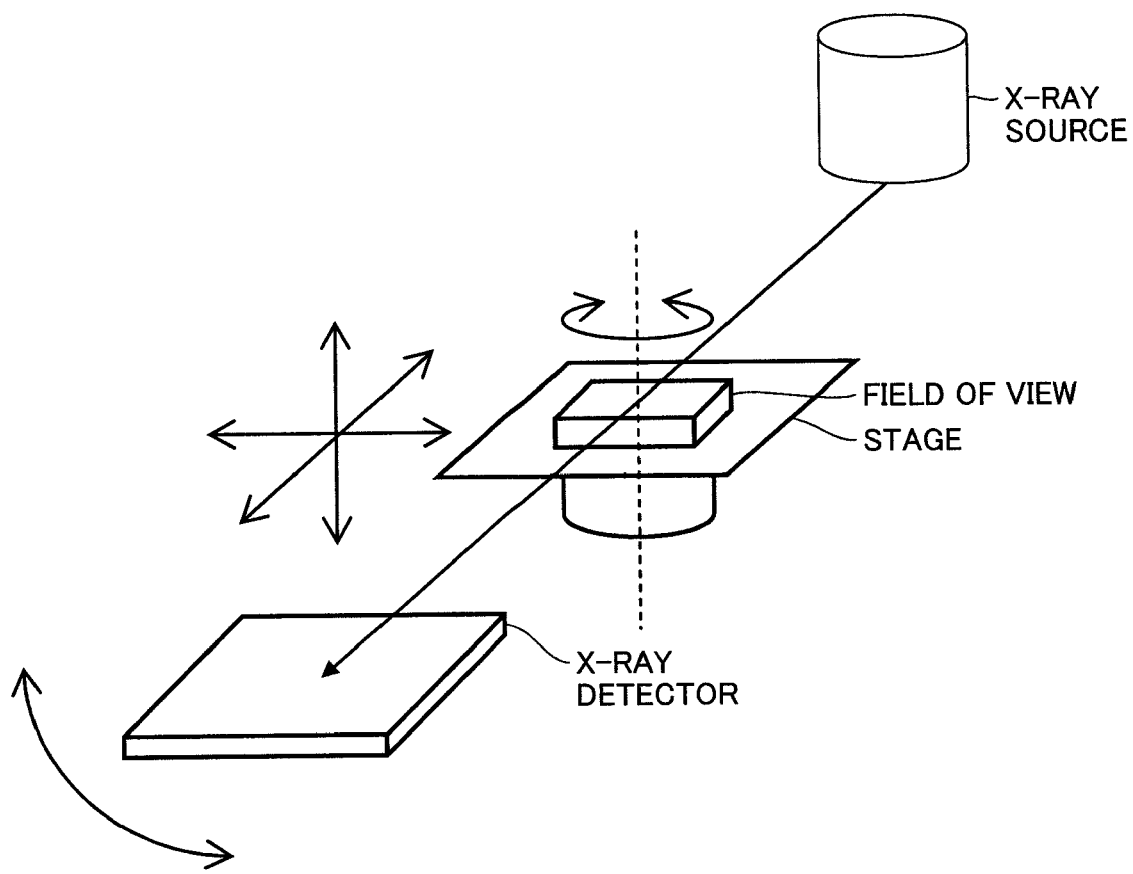
FIG. 21 shows a method for picking up an X-ray image in which a field of view (inspection object) is rotated according to one or more embodiments of the present invention.
Figure 22:
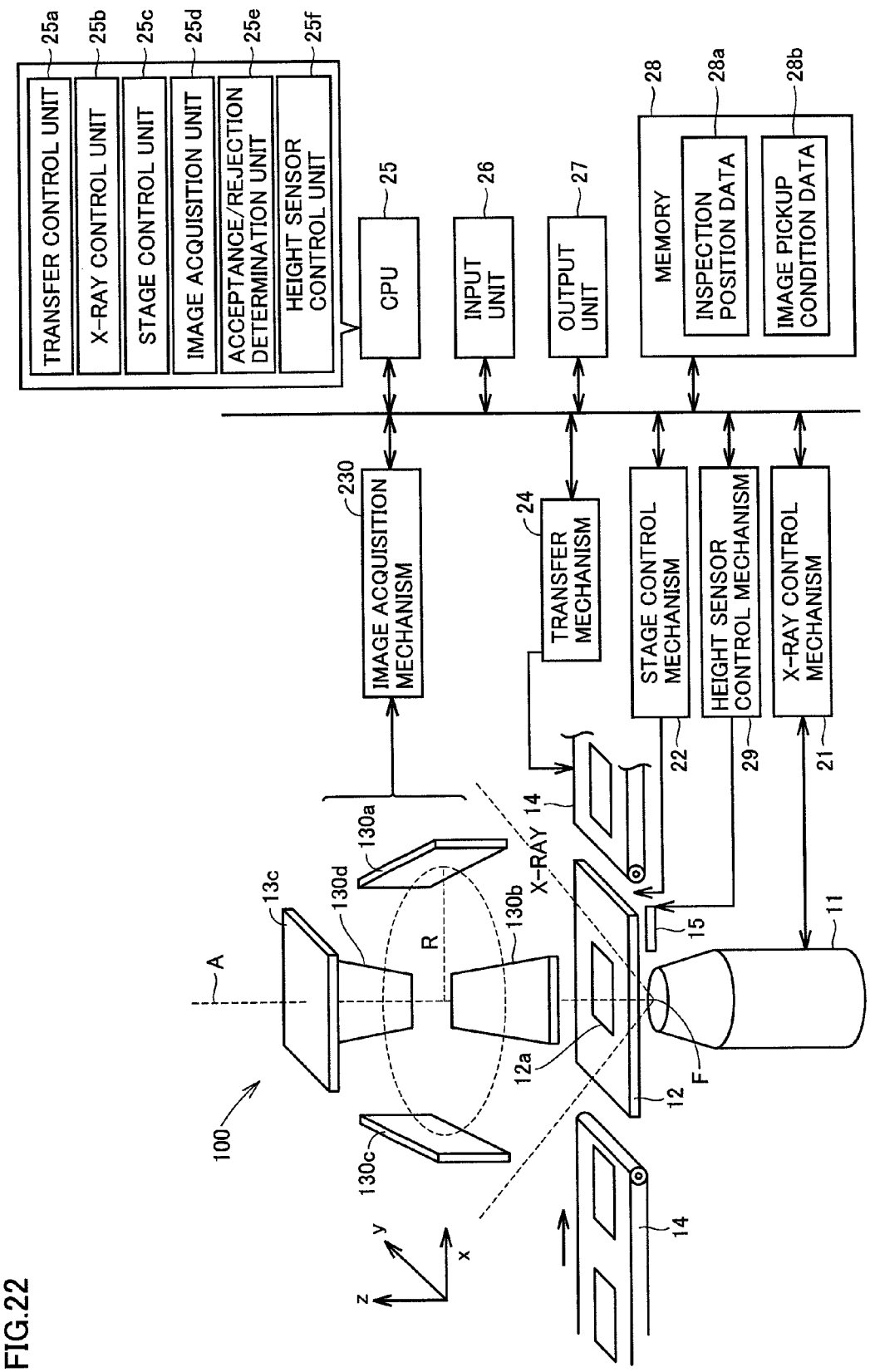
FIG. 22 shows an X-ray inspection apparatus in which three-dimensional inspection is conducted based on an X-ray image obtained by inclined X-ray detection means, so that both inspections can be conducted at high speed according to one or more embodiments of the present invention.
Figure 23:
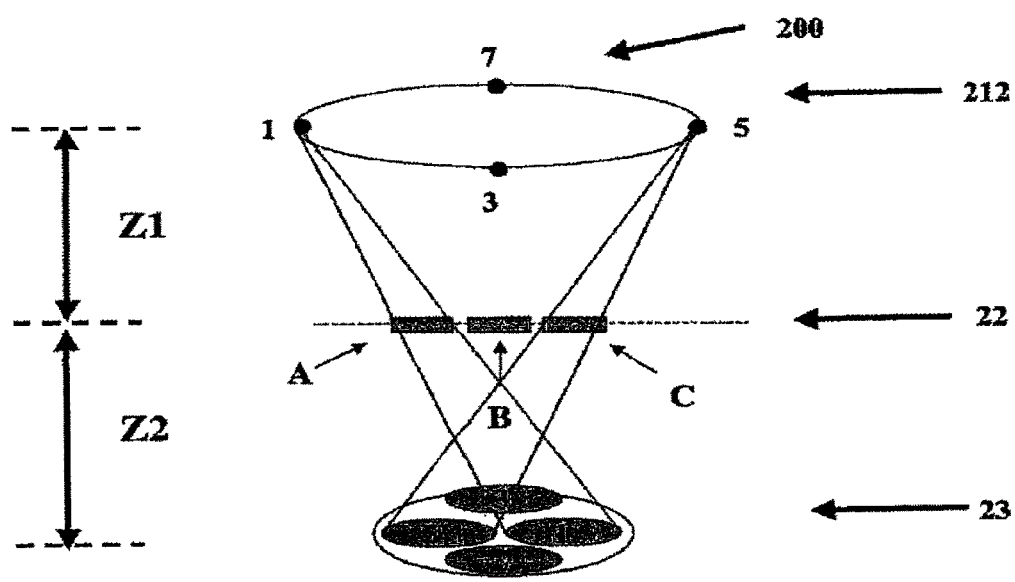
FIG. 23 shows an X-ray image pickup method using a scanning X-ray source and one X-ray detector fixed in position according to one or more embodiments of the present invention.
Figure 24:
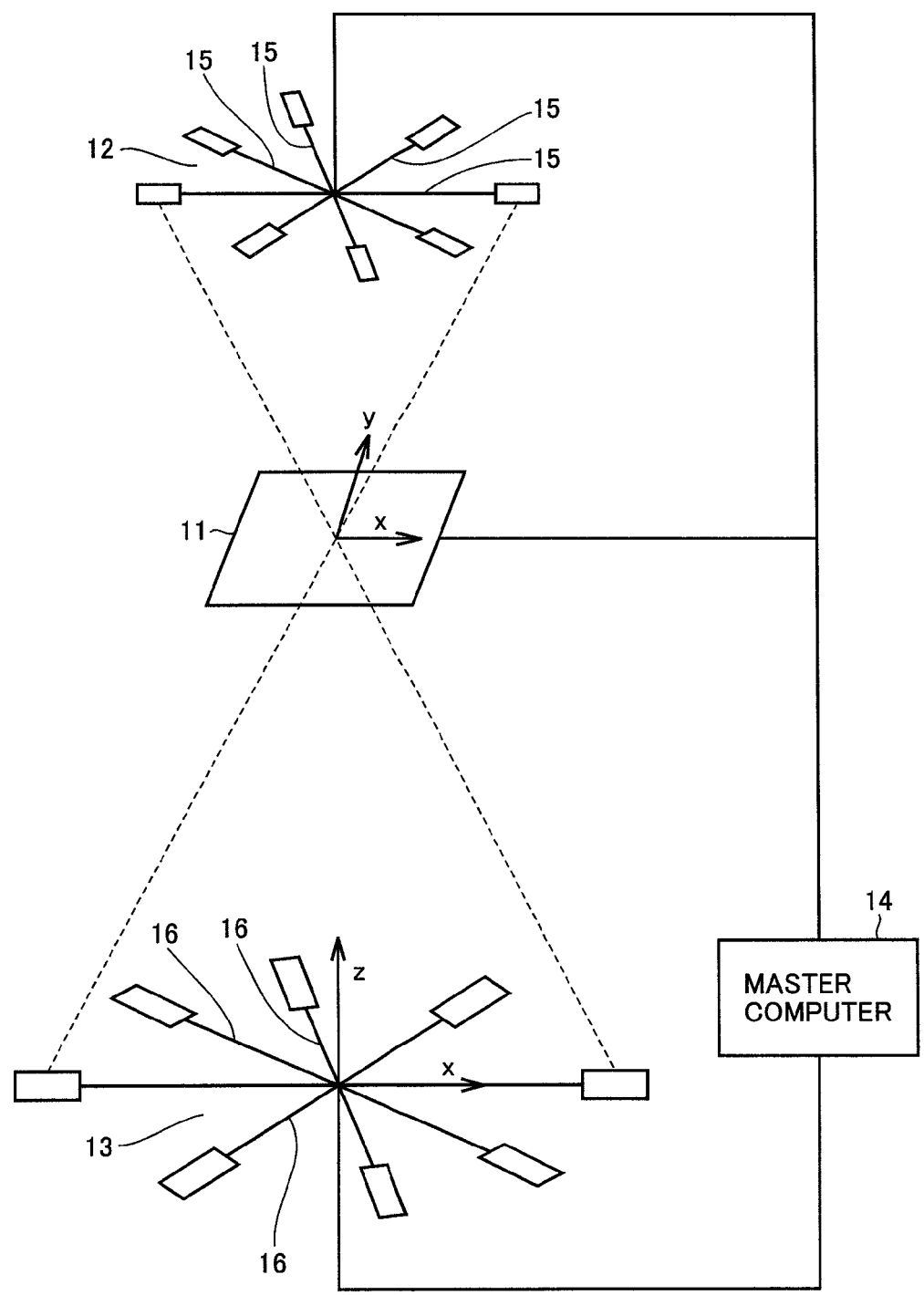
FIG. 24 shows an X-ray image pickup method using an apparatus including a plurality of movable X-ray sources and X-ray detectors as many as the X-ray sources according to one or more embodiments of the present invention.
Figure 25:
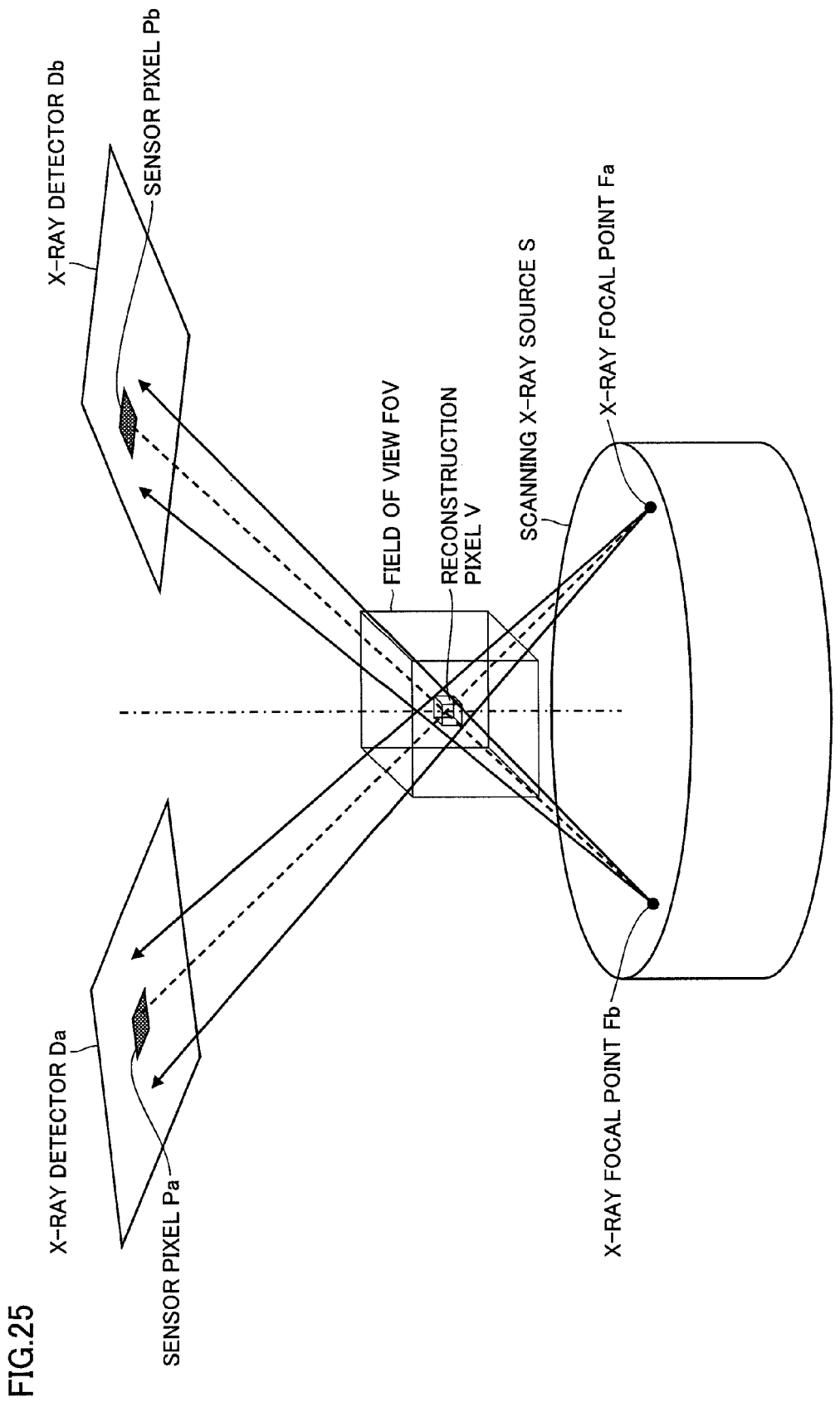
FIG. 25 illustrates an image reconstruction method according to one or more embodiments of the present invention.
Figure 26:
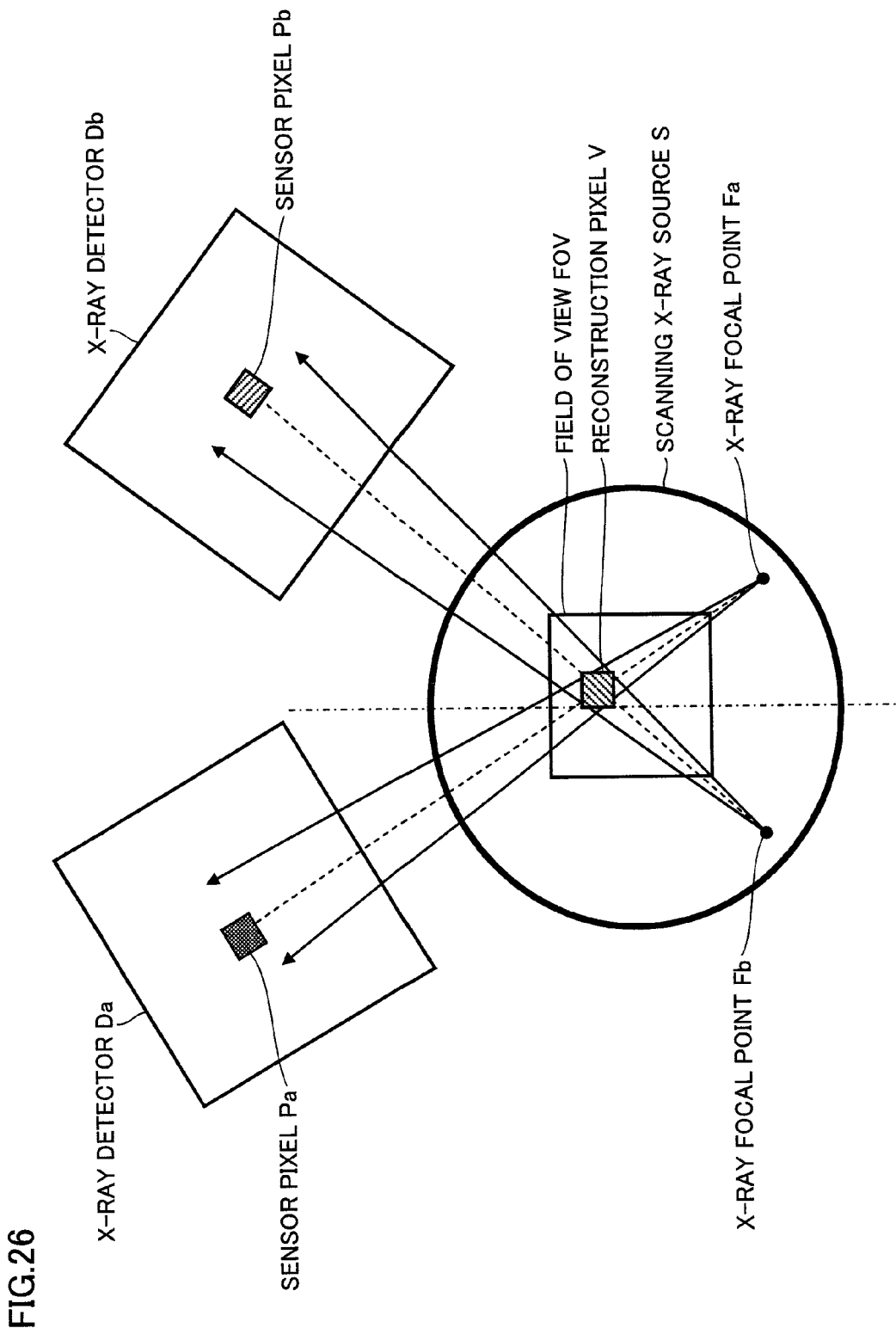
FIG. 26 shows arrangement of a reconstruction pixel V as an object of operation for reconstruction in a field of view FOV, X-ray focal points Fa and Fb, and X-ray detectors Da and Db, when viewed from above according to one or more embodiments of the present invention.

FIG. 20 is a timing chart illustrating time course of the CT image pickup and the image reconstruction processing in the flowchart of FIG. 19.

Namely, FIG. 20 illustrates steps of image reconstruction for the process of "reconstruct image of M fields of view" at step S540 in FIG. 19.

Again in FIG. 20, a symbol "FL1-A1" means a "transmitted image of field of view FL1 picked up in detector position A1." The same applies to the other numbers of fields of view FLm (m=1, . . . M) and the other signs of detectors (Ai, Bi: i=1, 2, . . . n) as well. In the example shown in FIG. 20, transmitted images from 3 (=number of detectors)×n directions are used.

The contents of subsequent processing are essentially similar to those illustrated in FIG. 16, and thus description thereof will not be repeated.

In the first embodiment and the modification of the first embodiment, image pickup time is reduced by moving not the large and heavy X-ray source but the X-ray detectors and the inspection object that can be moved relatively at high speed.

Further, a focal point position is scanned by the X-ray source in extremely short time while the X-ray detector stops, whereby images of a plurality of fields of view can be picked up.

Furthermore, with the simple mechanism of rectilinear movement of each constituent element, a distance of movement of the X-ray detector to a predetermined position is reduced and movement speed is increased. As a result, time for mechanical movement can be reduced to realize high-speed inspection.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

DESCRIPTION OF THE REFERENCE SIGNS

10 scanning X-ray source; 11 target; 12 deflection yoke; 13 electron beam convergence coil; 14 high-voltage power supply; 15 vacuum pump; 19 electron gun; 16 electron beam; 17 X-ray focal point position; 18 X-ray; 20 inspection object; 22 sensor base; 23 X-ray detector; 30 image acquisition control mechanism; 32 rotation angle control unit; 34 image data acquisition unit; 40 input unit; 50 output unit; 60 scanning X-ray source control mechanism; 62 electron beam control unit; 70 operation unit; 72 scanning X-ray source control unit; 74 image acquisition control unit; 76 3D image reconstruction unit; 78 acceptance/rejection determination unit; 80 stage control unit; 82 X-ray focal point position calculation unit; 84 image pickup condition setting unit; 90 memory; 92

X-ray focal point position information; 94 image pickup condition information; 100 X-ray inspection apparatus.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

The invention claimed is:

1. An X-ray inspection apparatus for picking up images of X-rays transmitted from directions that vary with inspection object areas of an object by using a plurality of detector planes, to perform reconstruction processing of an image of the inspection object areas of said object, comprising:
   an X-ray detector for picking up images in a plurality of detection positions;
   detector drive means for moving said X-ray detector to each of said plurality of detection positions;
   X-ray output means for scanning a focal point and outputting an X-ray;
   a plurality of said X-ray detectors;
   movement means for independently moving said X-ray detectors to said image pickup positions; and
   control means for controlling operation of said X-ray inspection apparatus, said control means comprising:
      image acquisition control means for controlling exposure timing of said X-ray detector and said detector drive means;
      X-ray output control means for controlling said X-ray output means; and
      image reconstruction process means for reconstructing image data on the plurality of inspection object areas based on data about intensity distribution of the X-rays transmitted through said inspection object areas and picked up by said plurality of detector planes,
   wherein said image acquisition control means and said X-ray output control means cause said X-ray detector to stop in one of a plurality of image pickup positions, and cause scanning of a focal point of said X-ray output means such that X-rays successively transmitted through said plurality of inspection object areas enter the X-ray detector in that image pickup position and cause image pickup for the different inspection object areas, and
   wherein said image acquisition control means and said X-ray output control means cause one of said plurality of X-ray detectors to stop in one of the plurality of image pickup positions, and cause performing of a process of scanning a focal point of said X-ray output means such that X-rays successively transmitted through said plurality of inspection object areas enter the X-ray detector in that image pickup position and causing image pickup for the different inspection object areas in parallel with a process of moving another X-ray detector different from said X-ray detector picking up images to another one of said plurality of image pickup positions.

2. The X-ray inspection apparatus according to claim 1, wherein said image reconstruction process means performs reconstruction processing in parallel with the process of moving said X-ray detector and the process of exposing said X-ray detector by said image acquisition control means and said X-ray output control means.

3. The X-ray inspection apparatus according to claim 1, wherein said detector drive means includes single-axis drive means for independently moving said plurality of X-ray detectors along a predetermined single-axis direction.

4. The X-ray inspection apparatus according to claim 1, wherein each of said detector planes of said plurality of X-ray detectors has a rectangular shape, and
wherein said detector drive means includes rotation means for rotating said plurality of X-ray detectors such that one end of each of said detector planes of each of said plurality of X-ray detectors intersects a direction directed to said X-ray output means in each of said image pickup positions.

5. The X-ray inspection apparatus according to claim 1, wherein the image reconstruction process means reconstructs the image data on said inspection object areas with an iterative method.

6. The X-ray inspection apparatus according to claim 1, wherein the image reconstruction process means reconstructs the image data on said inspection object areas with an analytical method.

7. An X-ray inspection method for picking up images of X-rays transmitted from directions that vary with inspection object areas of an object by using a plurality of detector planes, to perform reconstruction processing of an image of said inspection object areas, comprising:
   independently moving a plurality of X-ray detectors to a plurality of corresponding image pickup positions;
   scanning a focal point and outputting an X-ray;
   stopping one of said plurality of X-ray detectors in one of the plurality of image pickup positions which serves as one of said plurality of detector planes to perform a process of scanning a focal point of X-ray output means, wherein X rays successively transmitted through the plurality of inspection object areas enter the X-ray detector in that image pickup position and perform image pickup for the different inspection object areas in parallel with a process of moving another X-ray detector different from said X-ray detector picking up images to another one of said plurality of image pickup positions; and
   reconstructing image data on said inspection object areas based on data about intensity distribution of the X-rays transmitted through said inspection object areas and detected by said plurality of detector planes.

8. The X-ray inspection method according to claim 7, wherein said step of reconstructing image data is performed in parallel with said moving step and said the step of performing the process in parallel.

9. The X-ray inspection method according to claim 7, wherein in said independently moving step, said plurality of X-ray detectors are independently moved along a predetermined single-axis direction.

10. The X-ray inspection method according to claim 7, wherein each of said detector planes of said plurality of X-ray detectors has a rectangular shape, and
wherein said X-ray detectors rotate, during moving, such that one end of each of said detector planes of each of said plurality of X-ray detectors intersects a direction directed to said X-ray output means in each of said image pickup positions.

11. The X-ray inspection method according to claim 7, wherein in said step of reconstructing image data, the image data on said inspection object areas is reconstructed with an iterative method.

12. The X-ray inspection method according to claim 7, wherein in said step of reconstructing image data, the image data on said inspection object areas is reconstructed with an analytical method.

* * * * *